United States Patent [19]

Buchanan et al.

[11] 4,056,540
[45] Nov. 1, 1977

[54] 4-PHENYL-1,3-BENZODIOXANS

[75] Inventors: Ronald Leslie Buchanan, Fayetteville; Richard Anthony Partyka, Liverpool; Robert Ted Standridge, Cazenovia, all of N.Y.

[73] Assignee: Bristol-Myers Company, New York, N.Y.

[21] Appl. No.: 604,979

[22] Filed: Aug. 15, 1975

Related U.S. Application Data

[63] Continuation-in-part of Ser. No. 434,463, Jan. 1, 1974, abandoned.

[51] Int. Cl.$^2$ .............. C07D 319/08; C07D 405/06; C07D 405/12
[52] U.S. Cl. .............. 260/340.3; 260/293.58; 260/326.5 CA; 260/268 BQ; 260/268 BC; 424/248.54; 424/250; 424/248.56; 424/267; 424/274; 424/248.4; 424/278; 260/326.34; 544/148
[58] Field of Search .............. 260/340.3, 247.7 T, 260/268 BQ, 293.58, 326.5 D, 247.2 A, 268 BC, 326.34

[56] References Cited

U.S. PATENT DOCUMENTS

| 2,993,909 | 7/1961 | Lo | 260/340.3 |
| 3,117,978 | 1/1964 | Biel et al. | 260/340.3 |
| 3,149,108 | 9/1964 | Koo et al. | 260/247.7 T |
| 3,484,448 | 12/1969 | Kramer | 260/295.5 |

OTHER PUBLICATIONS

Dawksas, Chem. Abst. 71:12438e (1969).
Geigy, Chem. Abst. 57:16629c (1962).

*Primary Examiner*—Lorraine A. Weinberger
*Assistant Examiner*—Michael Shippen
*Attorney, Agent, or Firm*—Richard R. Lloyd

[57] ABSTRACT

Substituted 2-aminomethyl-4-phenyl-1,3-benzodioxans and derivatives thereof have been found to possess valuable anticonvulsant and antiarrhythmia activity in mammals. For example, cis-6-chloro-2-methylaminomethyl-4-phenyl-1,3-benzodioxan hydrochloride possesses potent anticonvulsant activity while cis-2-isopropylaminomethyl-4-phenyl-1,3-benzodioxan hydrochloride has potent antiarrhythmia activity.

20 Claims, No Drawings

4-PHENYL-1,3-BENZODIOXANS

CROSS-REFERENCE TO RELATED APPLICATIONS

This application is a continuation-in-part of a co-pending application, Ser. No. 434,463, filed Jan. 1, 1974 now abandoned.

BACKGROUND OF THE INVENTION

1. Field of the Invention

This invention relates to novel optionally substituted 2-aminomethyl-4-phenyl-1,3-benzodioxans and derivatives thereof which possess valuable anticonvulsant and antiarrhythmia activity.

2. Description of the Prior Art

Searches in the patent and scientific literature did not reveal the existence of any 2-aminoalkyl-4-phenyl-1,3-benzodioxans, 4-phenyl-1,3-benzodioxan-2-carboxylic acids or 4-phenyl-1,3-benzodioxan-2-carboxamides. The closest art found related to the isomeric 1,4-benzodioxan ring system.

a. V. Dauksas and A. Lastauksas, *Biol. Aktiv. Soedin.,* 286 (1968); *Chem. Abstr.* 71, 124348e (1969), which article reported the compounds having the structure

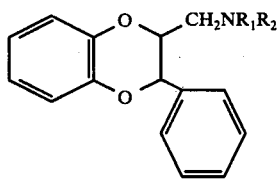

in which $-NR^1R^2$ are $-N(CH_3)_2$ or $N-(C_2H_5)_2$ as possessing local anesthetic activity.

b. F. Leonard and J. Koo, Belg. Patent 613,214, July 30, 1962; *Chem. Abstr.*, 57, 16629c (1962), which article reported the compounds having the structure

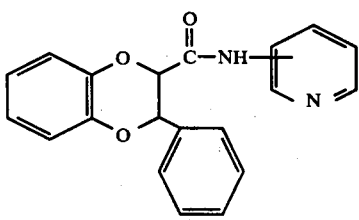

as possessing sedative and tranquilizing activity.

c. U.S. Pat. No. 3,484,448 reports the compounds having

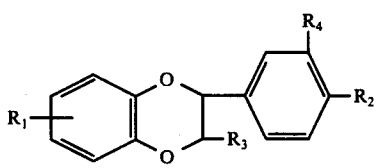

wherein
$R_1$ represents H, OH, $RCH_2$, RCHOH, RCO, alkoxy of 1-5 carbon atoms, or $-O-(CH_2)_n-NR'R''$;
$R_2$ represents H, OH, $CH_3$, alkoxy of 1-5 carbon atoms, or $-O-(CH_2)_n-NR'R''$;
$R_3$ represents H or alkyl of 1-6 carbon atoms;
$R_4$ represents H, OH, $CH_3O$, or together with $R_2$, methylenedioxy;
R represents H or $CH_3$;
n is 2 or 3 and
R' and R'', being the same or different, represent alkyl of respectively 1-3 carbon atoms, or together with the N-atom, a 5- or 6-membered heterocyclic ring, and wherein the group $-O-(CH_2)_n-NR'R''$ has a total of 4-8 carbon atoms as possessing cholesterol-level-lowering activity.

SUMMARY OF THE INVENTION

Compounds having the formula

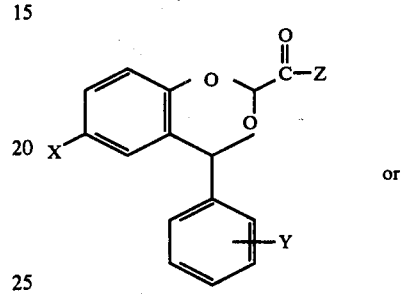

or

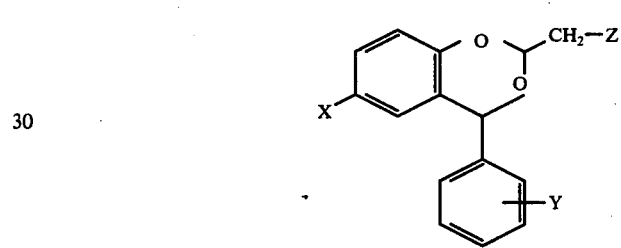

in which X and Y are alike or different and are H, F, Cl, Br, $CF_3$ or nitro, Z is a radical having the formula

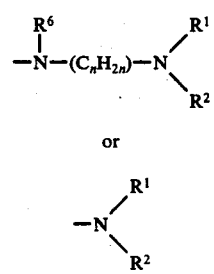

or $$-N\begin{matrix}R^1\\R^2\end{matrix}$$

in which $R^6$ is H, (lower)alkyl or phenyl, $R^1$ and $R^2$ are alike or different and each is H, lower alkyl, cyclolower-alkyl or when taken together with the nitrogen a heterocyclic ring having the formula

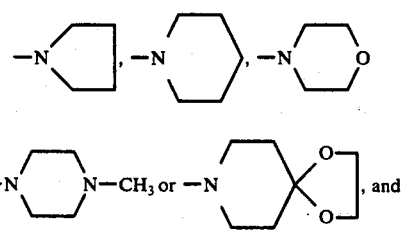

$n$ is an integer of 1 to 4 inclusive;
or a pharmaceutically acceptable acid addition salt thereof.

COMPLETE DISCLOSURE

Compounds having the formula

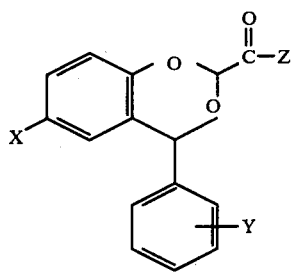

or

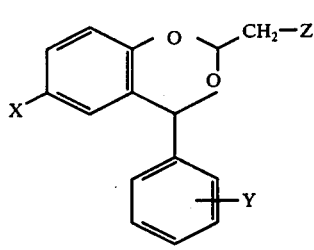

in which X and Y are alike or different and are H, F, Cl, Br, $CF_3$ or nitro, Z is a radical having the formula

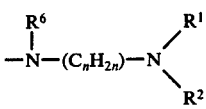

or

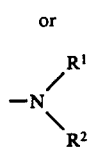

in which $R^6$ is H, (lower)alkyl or phenyl, $R^1$ and $R^2$ are alike or different and each is H, lower alkyl, cycloloweralkyl or when taken together with the nitrogen a heterocyclic ring having the formula

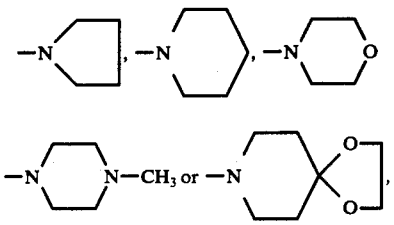

and n is an integer of 1 to 4 inclusive;
or a pharmaceutically acceptable acid addition salt thereof have been found to possess useful anticonvulsant and antiarrhythmia activity in mammals. The compounds are specifically useful in the treatment of grand and petite mal epileptic-like convulsions and are useful as therapeutic and prophylactic agents in the treatment of cardiac arrhythmia.

For the purpose of this disclosure, the terms lower alkyl, cycloloweralkyl and lower alkoxy are radicals containing 1 to 6 carbon atoms. The term "pharmaceutically acceptable acid addition salt" includes all those salts commonly employed in pharmaceuticals which are prepared by the reaction of an amine with a pharmaceutically acceptable acid. Such acids include, among others, acetic, hydrochloric, sulfuric, maleic, phosphoric, nitric, hydrobromic, ascorbic, malic and citric acid.

A preferred embodiment of the present invention is the compound having the formula

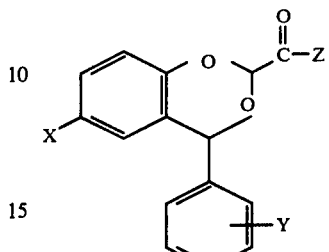

or

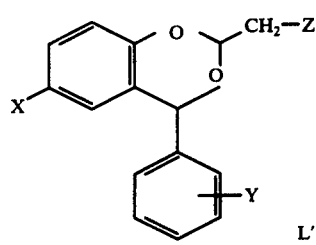

L' in which X and Y are alike or different and are H, F, Cl, Br, $CF_3$ or nitro, Z is a radical having the formula

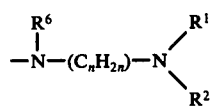

or

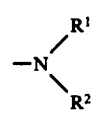

in which $R^6$ is H, (lower)alkyl or phenyl, $R^1$ and $R^2$ are alike or different and each is H, lower alkyl, cyclolower alkyl or when taken together with the nitrogen a heterocyclic ring having the formula

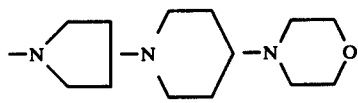

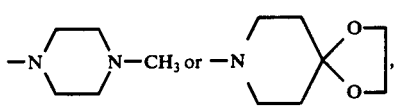

and n is an integer of 1 to 4 inclusive;
or a pharmaceutically acceptable acid addition salt thereof.

Another preferred embodiment is a compound having the formula

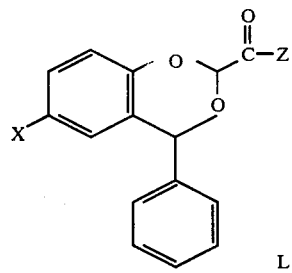

in which X and Y are alike or different and are H, F, Cl, Br, CF₃ or nitro, Z is a radical having the formula

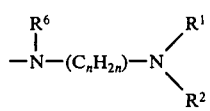

or

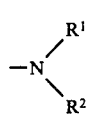

in which R⁶ is H, (lower)alkyl or phenyl, R¹ and R² are alike or different and each is H, lower alkyl, cycloloweralkyl or when taken together with the nitrogen a heterocyclic ring having the formula

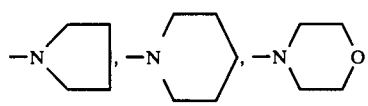

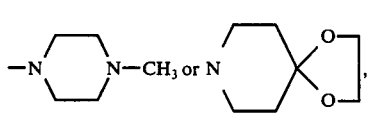

and n is an integer of 1 to 4 inclusive;
or a pharmaceutically acceptable acid addition salt thereof.

A more preferred embodiment is a compound of formula L¹ in which X and Y are alike or different and are H, F, Cl, Br, CF₃ or NO₂, and Z is a radical having the formula

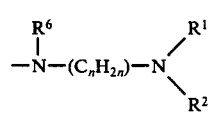

or

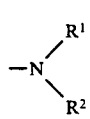

in which R⁶ is H, (lower)alkyl or phenyl, R¹ and R² are alike or different and each is H, lower alkyl, cycloloweralkyl or when taken together with the nitrogen a heterocyclic ring having the formula

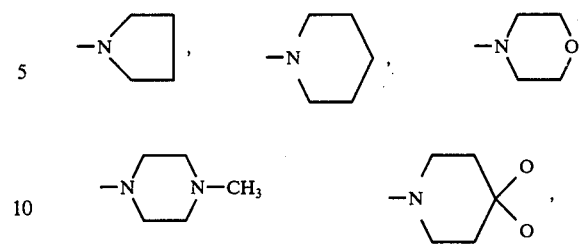

and n is an integer of 1 to 4 inclusive;
or a pharmaceutically acceptable acid addition salt thereof.

A most preferred embodiment is the compound having the formula

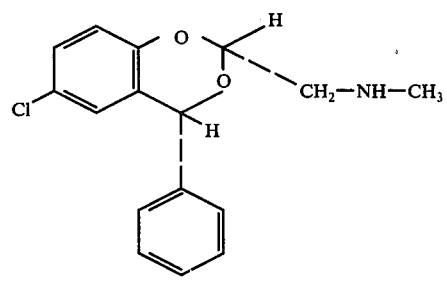

or the hydrochloride salt thereof.

A most preferred embodiment is the compound having the formula

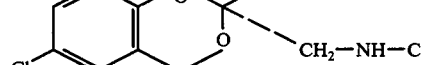

or the hydrochloride salt thereof.

A most preferred embodiment is the compound having the formula

or the hydrochloride salt thereof.

A most preferred embodiment is the compound having the formula

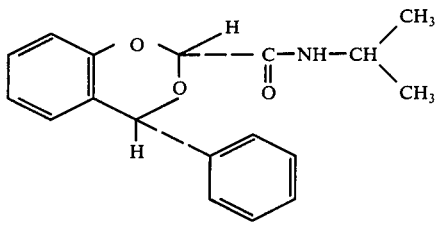

or the hydrochloride salt thereof.

A most preferred embodiment is the compound having the formula

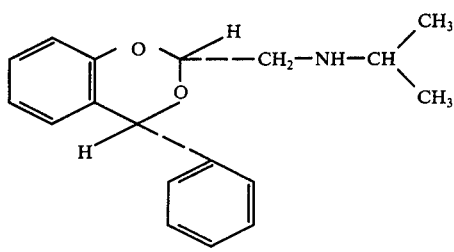

or the hydrochloride salt thereof.

A most preferred embodiment is the compound having the formula

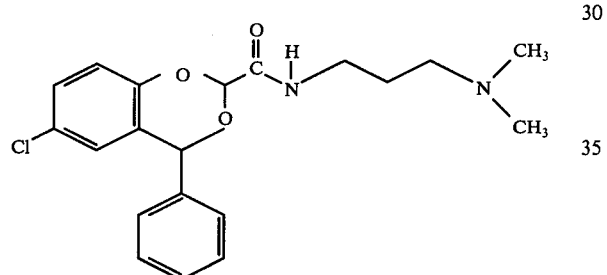

or a pharmaceutically acceptable acid addition salt thereof.

A most preferred embodiment is the compound having the formula

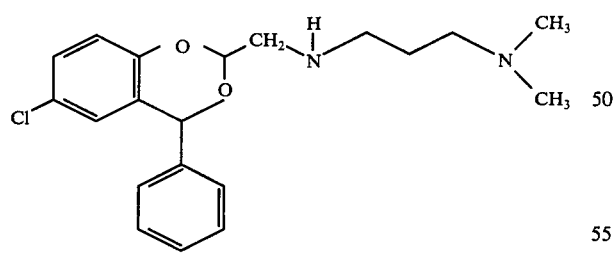

or a pharmaceutically acceptable acid addition salt thereof.

Also a preferred embodiment is the essentially pure cis and trans isomers of the compounds described supra.

The compounds of structure L and $L^1$ contain a dioxan ring and two asymmetric carbon atoms and may thus exist as both geometrical and optical isomers. Two geometrical isomers, in approximately equal ratios, were typically obtained by our synthetic sequence. These were readily separated by fractional crystallization of the acids (IV) or the amides (V) from a suitable solvent. Nitromethane or a mixture of $CCl_4$ and ethanol-free $CHCl_3$ were preferred.

The structures of the geometric isomers were assigned unambiguously by 100 MHz nmr. See example 1c for a detailed discussion. Of the four possible isomers VII through X, VII and IX were shown to be the ones obtained by our procedures, and are referred to as cis and trans, respectively. Although each of these isomers may exist as a racemic mixture, no attempt was made at this time to resolve these racemates. However, all such isomers are within the scope of this invention.

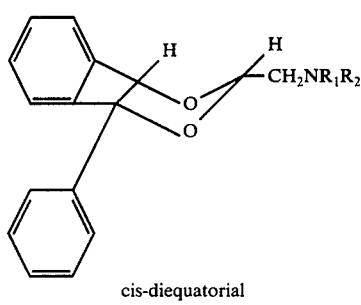

cis-diequatorial

VII

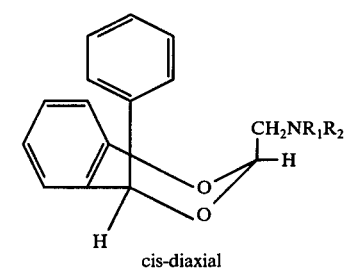

cis-diaxial

VIII

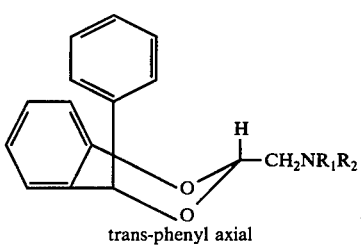

trans-phenyl axial

IX

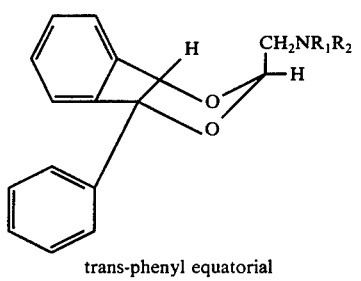

trans-phenyl equatorial

X

Shown below is the sequence employed to synthesize the compounds L:

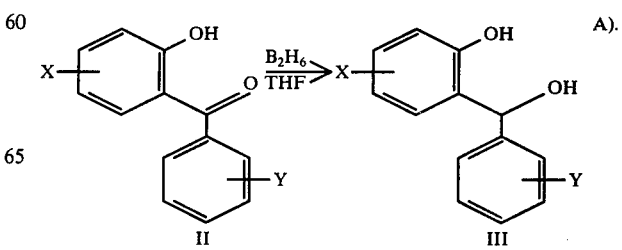

A).

A)
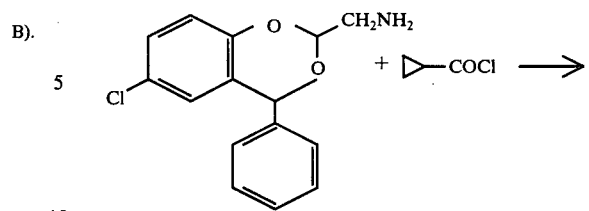

B)
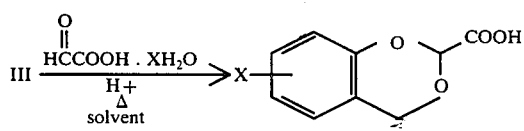

IV

C)
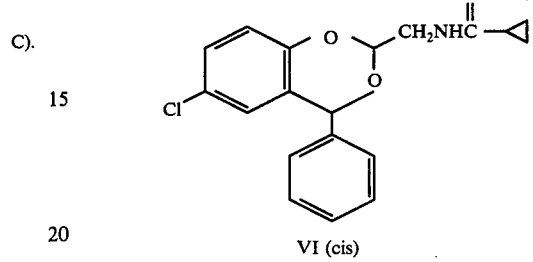
VI (cis)

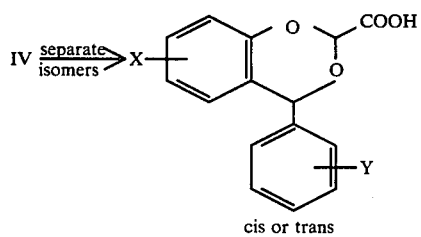
IV
cis or trans

VI $\xrightarrow{B_2H_6}{THF}$

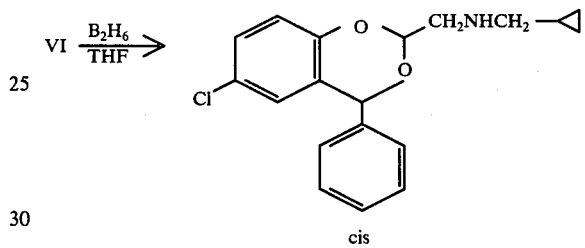
cis

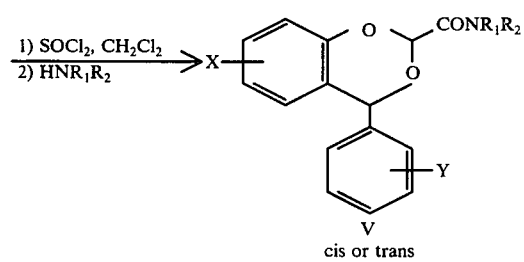
V
cis or trans

D). Compounds with a halogen in the 6-position could be easily dehalogenated catalytically. This could be done in the presence of another halogen elsewhere in the molecule.

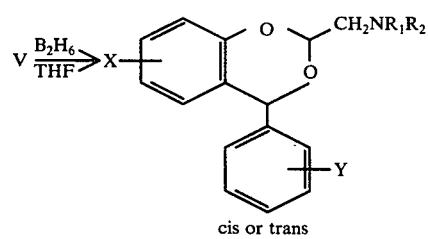
cis or trans

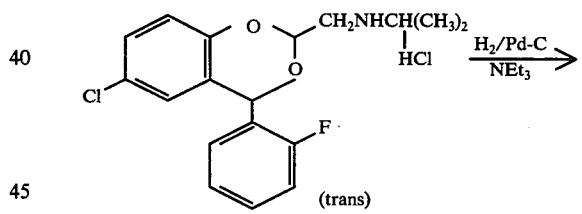
(trans)

Primary or secondary amines L could be methylated by the Eschweiler-Clarke[1] procedure. This method was particularly advantageous in preparing amines with two different substituents:

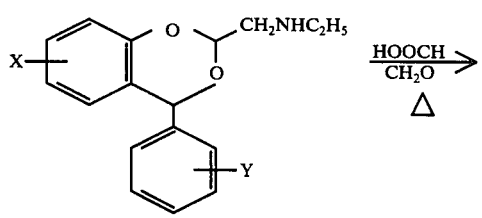

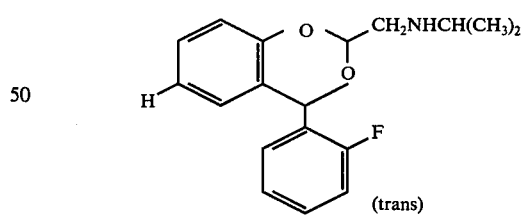
(trans)

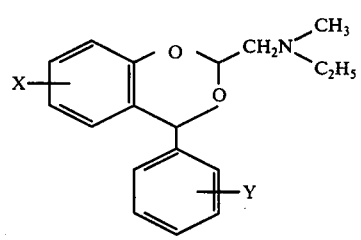

1. M. L. Moore, *Organic Reactions*, 5, 301 (1949).

The compounds L likewise provided other amines through amidation and reduction:

Compound III (X = 5-Cl, Y = H) has been prepared, in unspecified yield, with NaBH$_4$ as reducing agent. This method was found to be not amenable to scaleup. Toluene, and particularly dioxane, were preferred solvents in the condensation of III with glyoxylic acid. Diborane in THF smoothly reduced the amides V to the amines I. Other common reducing agents (LiAlH$_4$, AlH$_3$) were ineffective.

The objectives of the present invention have been achieved, by the provision according to the present invention of the process for the preparation of the compound having the formula

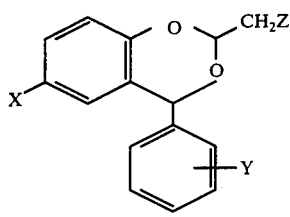

in which X and Y are alike or different and are H, F, Cl, Br, $CF_3$ or nitro, Z is a radical having the formula

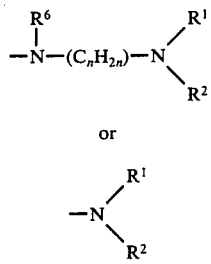

in which $R^6$ is H, (lower)alkyl or phenyl, $R^1$ and $R^2$ are alike or different and each is H, lower alkyl, cycloloweralkyl or when taken together with the nitrogen a heterocyclic ring having the formula

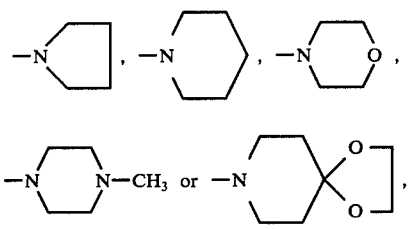

and n is an integer of 1 to 4 inclusive;
which process comprises the consecutive steps of
A. treating a compound having the formula

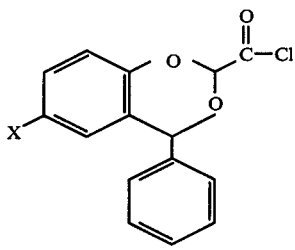

with an amine having the formula

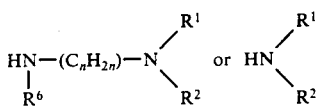

in which $R^1$, $R^2$ and $R^6$ are as defined above to produce the compound having the formula

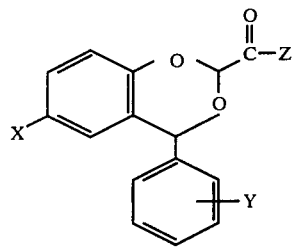

in which Z is defined as above; and
B. treating a compound having the formula

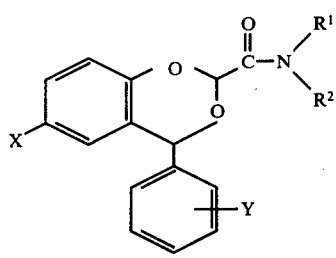

XXXX in which X, Y and Z are as defined above; with diborane in tetrahydrofuran, dioxane, diethyl ether and the like, but most preferably tetrahydrofuran, in a ratio of 1 mole of compound XXXX to at least 3 moles of diborane and preferably in a ratio of 1 mole of XXXX to 4 to 8 moles of diborane, and most preferably in a ratio of 1 mole of XXXX to 5.5 moles of diborane, with refluxing for at least 10 hours, and preferably 15 to 25 hours.

The compounds L and $L^1$ of the instant invention have been found to be effective agents in the prevention of tonic convulsions and the therapeutic and prophylactic treatment of cardiac arrhythmia.

Table I illustrates the results obtained on four compounds; e.g., BL-3069 (1B); BL-3168 (8B); BL-3396 (22B); and BL-3681A (28B) as compared to 4 reference agents in the control of convulsions.

Table I
Anticonvulsant Profile of BL-3069, BL-3168, BL-3396, BL-3681 and Reference Agents in the Mouse and Rat

| | ED50, mg/kg po[1] | | | | | | |
|---|---|---|---|---|---|---|---|
| | Maximal Electroshock[2] | | Audiogenic Seizure[3] | Pentylenetetrazole | | | LD50[6] |
| Compound | Mouse | Rat | Mouse | Mouse | | Rat | Mouse |
| BL-3069 (1B) | 25 | >20 | — | 12[4] | | >40[5] | 300 |
| BL-3168 (8B) | 10 | 15 | 2.5 | 5 | >50[5] | >40 | 300 |
| BL-3396 (22B) | 10 | 10 | 2.5 | 3 | >50 | >40 | 400 |
| BL-3681A (28B) | 12 | 15 | 10 | 12 | >50 | >40 | 300 |
| Diphenylhydantoin Na | 10 | 30 | 10 | 20 | >50 | 40 | 540 |
| Diazepam | 6 | 10 | 0.5 | 2 | 2 | 5 | 1400 |
| Phenobarbital Na | 10 | 8 | 2.5 | 8 | 15 | 20 | 265 |
| Trimethadione | >400 | 300 | 150 | 200 | 400 | 100 | 2170 |

[1]Test compounds including reference agents were administered orally either as water solutions or as fine suspensions in Tween by gastric intubation 60 min prior to the test. There were at least 3 animals per dose.
[2]Maximal Electroshock Test - Animals were subjected to an 80mA shock of 0.5 sec duration by a means of corneal electrodes using the

Table I-continued
Anticonvulsant Profile of BL-3069, BL-3168, BL-3396, BL-3681 and Reference Agents in the Mouse and Rat

| | ED50, mg/kg po[1] | | | | | LD50[6] |
|---|---|---|---|---|---|---|
| | Maximal Electroshock[2] | | Audiogenic Seizure[3] | Pentylenetetrazole | | |
| Compound | Mouse | Rat | Mouse | Mouse | Rat | Mouse | specially designed apparatus manufactured by Wahlquist Instrument Co. Prevention of tonic extension by hind limbs was used as a criterion for drug effect.

[3]Audiogenic Seizures - Mice, which were genetically bred for the susceptability to sound induced seizures (O'Grady Farms) were placed into the sound attenuated box and exposed to a 120 sec sound stimulus of 85 db and 10,000 c/sec frequincy. Prevention of tonic extension of hind limbs was used as a criterion for drug effect.

[4]Pentylenetetrazol Infusion (Mouse) - The procedure originally described by Orloff, M. H. et al., Proc. Soc. Exp. Biol. 70:254 (1949) and adopted by our laboratories was used.

[5]Pentylenetetrazol Standard Dose - Animals were challenged with a standard dose of pentylenetetrazol (125 mg/kg ip) following pretreatment with a test compound. Prevention of lethality was used as criterion for drug effect.

[6]Acute Toxicity (Mouse) - Animals were observed for a period of 24 hours following drug administration.

As can be seen from the table, BL-3069, BL-3168, BL-3396 and BL-3681A were effective blocking agents of tonic convulsions induced by maximal electroshock and audiogenic seizures, while they proved practically ineffective against pentylenetetrazole.

In the latter procedure, they merely antagonized the tonic convulsant component of the stimulatory pattern while they were ineffective against clonic convulsions and death (see footnotes 4 and 5 in Table I, respectively). Thus, it is apparent that they mimicked diphenylhydantoin with respect to the activity profile. The known pentylenetetrazol antagonisits (diazepam, trimethadone and phenobarbital) were able to antagonize all the excitatory signs induced by pentylenetetrazol, i.e., clonic and tonic convulsions and lethality, however, this was not the case with the BL-compounds.

Thus, it can be concluded that the compounds L and L[1] can be classified as diphenylhydantoin-like compounds on the basis of the laboratory results.

The dose of the compounds L and L[1] in man is 25 to 500 mg three to four times a day depending upon the severity of the grand mal and/or petite mal seizures and the compound L so used. The patient must be titrated with the particular compound until a convulsion suppressing does is found. The compounds can be used as therapeutic or prophylactic agents.

The compounds were also tested in dogs for their reversion activity in ouabain-induced arrhythmia.

Anesthetized dogs were used for the production of ouabain-induced ventricular arrhythmias. The arrhythmia consisted of a nodal or ventricular tachycardia. The procedure used to establish the arrhythmia as well as the criteria employed to determine anti-arrhythmic activity generally was that employed by Lucchesi et al.[1]

1. Lucchesi, B. L. and H. F. Hardman: The influence of dichloroisoproterenol (DCI) and related compounds upon ouabain and acetylstrophanthidin induced cardiac arrhythmias. J. Pharmacol. Exp. Therap., 132:372, 1961.

Anti-arrhythmic activity of the compounds was determined by rapid intravenous injection and compared to lidocaine, disopyramide and aprindine The average prolonged reversion doses are shown below:

TABLE I
Effect of Various Substituted Phenylbenzodioxans on Ouabain-Induced Cardiac Arrhythmias in the Anesthetized Dog

| Compound BL No. | X | C=Y | R | Isomer | I. V. Reverting Dose, mg/kg[a] |
|---|---|---|---|---|---|
| 3168 | Cl | $CH_2$ | $-CH_3$ . HCl | cis | >10 (N=1) Decrease in mean aortic pressure of 20 mmHg. |
| 4093 | Cl | C=O | $-CH_3$ . HCl | cis | >10 (N=1) |
| 3100 | Cl | $CH_2$ | $-CH_3$ | trans | >10 (N=1) Decrease in mean aortic pressure of 50 mmHg. |
| 3167 | Cl | C=O | $-CH_3$ | trans | >10 (N=1) |
| 3418 | H | $CH_2$ | $-CH(CH_3)_2$ . HCl | cis | 3-5 (N=2) |
| 3379 | Cl | $CH_2$ | $-CH(CH_3)_2$ . HCl | trans | >10 (N=1) |
| 3374 | Cl | C=O | $-CH(CH_3)_2$ | trans | >10 (N=1) |
| 3394 | H | $CH_2$ | $-CH(CH_3)_2$ . HCl | trans | ~10 (N=1) Accompanied by a progressive fall in aortic blood pressure. |
| 4981A | H | C=O | $-(CH_2)_3-N(CH_3)_2$ . HCl | cis | >10 (N=2) |
| 4932A | Cl | C=O | $-(CH_2)_3-N(CH_3)_2$ . HCl | trans | Transient reversion at 10 mg/kg, transient 50 mmHg fall in aortic blood pressure (N=2). |
| 4971A | Cl | C=O | $-(CH_2)_3-N(CH_3)_2$ . HCl | cis | 5 (N=3) No appreciable effect on aortic blood pressure. |
| Lidocaine | | | | | 6.4 ± 1.4 (N=8) |
| Disopyramide | | | | | 4.5 ± 1.3 (N=6) |
| Aprindine | | | | | 2.46 ± 0.83 (N=5) |

N=Number of dogs.

[a]IV ED100 refers to the dose of drug resulting in total reversion to a normal sinoatrial rhythm for greater than 30 mins., unless otherwise noted.

The compounds of the present invention are useful in the treatment of caridac arrhythmia in mammals, including man, as prophylactic or therapeutic agents in doses in the range of 0.25 mg. to 3.0 mg./kg. up to 3 or 4 times a day.

PREFERRED EMBODIMENTS

EXAMPLE 1

Cis-and Trans-6-Chloro-4-Phenyl-1,3-Benzodioxan-2-Carboxylic Acids

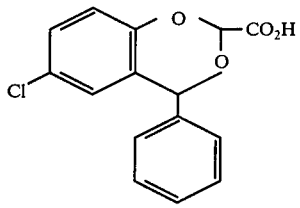

a. 5-Chloro-2-hydroxybenzhydrol[2]

5-Chloro-2-hydroxybenzophenone (100.0 g, 0.429 mole) was dissolved with stirring, under anhydrous conditions, in 1 liter of anhydrous THF (tetrahydrofuran) contained in a 5 l. flask. The flask was immersed in an ice-water bath, the solution was stirred vigorously, and 450 ml (0.45 mole) of diborane in THF soln (1M as $BH_3$) was immediately added from a dropping funnel as rapidly as maintaining control of the reaction would allow; about 4 minutes was required. Foaming occurred and the color of the reaction mixture deepened, then lightened. After addition, the colorless solution was stirred in the cooling bath for 15 minutes and was then poured slowly, cautiously, and with good stirring onto a mixture of cracked ice and 700 ml of 5% HCl soln.

The insoluble material was extracted out with 3 portions of ether; the combined extracts were washed with dilute $NaHCO_3$ soln (2 portions), water (1 portion) and saturated brine (1 portion) and dried over anhydrous $MgSO_4$. Evaporation of the solvents gave an oil which was taken up in hot cyclohexane; the solvent was evaporated and the residue was stripped in vacuum. The oil thus obtained was dissolved i 1200 ml of hot cyclohexane; the solution was filtered, seeded, and allowed to stand at room temperature.

The solid was filtered, washed with cyclohexane, and air-dried. Light cream-colored crystals, mp 93°–95°, were obtained. The yield was 64.5 g (62%).

2. G. N. Walker and R. T. Smith, *J. Org. Chem.*, 36, 305 (1971).

b. cis-and trans-6-Chloro-4-phenyl-1,3-benzodioxan-2-carboxylic acids

A solution of 118 g (0.525 mole) of 5-chloro-2-hydroxybenzhydrol, 83 g (0.822–0.902 mole) of glyoxylic acid hydrate[3], and 0.7 g of p-toluene-sulfonic acid hydrate in 1000 ml of dioxane was stirred and heated to boiling. Solvent was distilled and fresh dioxane was added to maintain the pot volume at ca. 1 l. Distillation was continued for 12 hrs.; a total of 3.7 l. of distillate was collected. The reaction mixture then cooled to room temperature over a period of 8 hrs.

3. The water content of this material is not specified by the manufacturer, Aldrich Chemical Co. Karl Fisher moisture determination on one lot indicated the presense of 1.0–1.5 moles $H_2O$/mole compound.

The reaction mixture was stripped of dioxane in vacuum; the residue was dissolved in ether and the solution was washed with two portions of water. The ether solution was then extracted with 6 portions of dilute $NaHCO_2$ solution and discarded. The combined $NaHCO_3$ extracts were acidified with conc. HCl and the insoluble material was extracted out with ether. The ether solution was washed with water (3 portions) and saturated brine (2 portions) and dried over anhydrous $Na_2SO_4$. Evaporation of the solvent gave 140 g (92%) of a solid mixture of acids.

This material was combined with 77g from a pervious run (total, 217 g) and the mixture was stirred and boiled with 500 ml of $CCl_4$ and 1800 ml alcohol-free $CHCl_3$. The insoluble material was filtered, washed with two 250 ml portions of boiling $CHCl_3$, and dried in vacuum to yield 20.2 g of pure, colorless cis-6-chloro-4-phenyl-1,3-benzodioxan-2-carboxylic acid, mp 191°–193°. Upon 12 hr's standing at room temperature, the filtrate deposited a solid; this was filtered, washed with $CCl_4$, and dried to provide 62.7 g of less pure cis-acid. The mother liquor was reserved for recovery of the trans-isomer. The impure cis-acid was recrystallized from nitromethane to give an additional 37.6 g of cis-acid, m.p. 192°–193°. The total yield was 56.8 g (24.5% or 49% of available cis-isomer). Nuclear Magnetic Resonance Spectra [NMR ($CDCl_3$-DMSO)], d$\delta$6.62 (d, 1H, C(5)H, cis; 5.65 ppm (s, 1H, C(2)H, cis).

Anal. Calc'd for $C_{15}H_{11}ClO_4$: C, 61.98; H, 3.81; Cl, 12.20. Found: C, 61.82; H, 3.74; C1, 12.13.

Upon standing at room temperature, the mother liquor and washings from isolation of the cis-isomer deposited additional solid. This was filtered and washed with $CCl_4$ to give 28.6 g of pure trans-6-chloro-4-phenyl-1,3-benzodioxan-2-carboxylic acid; m.p. 153°–154.5°. The filtrate provided a second crop, 12.3 g, m.p. 153°–154°. The mother liquor was discarded. The total yield of trans-acid was 40.9 (17.3% or 34.6% of available trans-isomer). NMR ($CDCl_3$-DMSO), $\delta$6.85 (d, 1H, C(5)H, trans); 5.42 ppm (s, 1H, C(2)H, trans).

Anal. Calc'd for $C_{15}H_{11}ClO_4$: C, 61.98; H, 3.81; Cl, 12.20. Found: C, 62.25; H, 4.08; Cl, 12.14.

c. Methyl esters and assignment of structures 1. cis-Methyl 6-chloro-4-phenyl-1,3-benzodioxan-2-carboxylate To an ether solution of cis-6-chloro-4-phenyl-1,3-benzodioxan-2-carboxylic acid (2.14 g, 7.36 mmoles), chilled in an ice bath, was added an ethereal solution of diazomethane until the yellow color of the diazomethane was no longer discharged. The solution was stirred in the ice bath for 10 minutes at room temp. for 10 minutes, and finally at 35° for 15 minutes. The ether solution was washed with dil.$NaHCO_3$ solution (2 portions), water (2 portions), and saturated brine (1 portion), and dried over anhydrous $Na_2SO_4$. The solvent was evaporated to yield a solid which was recrystallized from benzene-Skellysolve B (essentially n-hexane). The yield was 1.71 g (76%); m.p. 129.5°–131°. NMR ($CDCl_3$), $\delta$6.6 (d, 1H, C(5)H, cis); 5.65 ppm (s, 1H, C(2)H, cis).

Anal. Calc'd. for $C_{16}H_{13}ClO_4$: C, 63.07; H, 4.30; Ca, 11.63. Found: C, 63.24; H, 4.59; Cl, 11.79.

2. trans-Methyl 6-chloro-4-phenyl-1,3-benzodioxan-2-carboxylate.

A similar procedure to that described in part 1 above, utilizing 2.08 g (7.14 mmoles) of trans-6-chloro-4-phenyl-1,3-benzodioxan-2-carboxylic acid, provided 1.79 g (82%) of trans-ester; m.p. 103.5–106.5%. NMR (CDCl$_3$), δ6.85 (d, 1H, C(5)H, trans); 5.5 ppm (s, 1H, C(2)H, trans)

Anal. Calc'd. for C$_{16}$H$_{13}$ClO$_4$: C, 63.07; H, H, 4.30; Cl, 11.63. Found: C, 63.40; H, 4.60; Cl, 11.31.

3. Assignment of structures

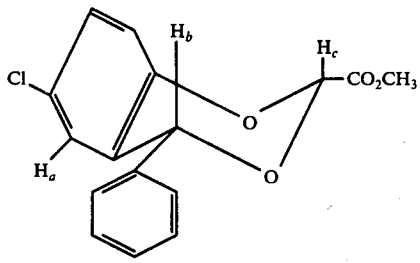

A

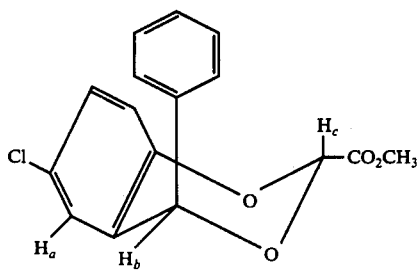

B

The structures of the two methyl esters were assigned unambiguously on the basis of their 100 MHz nmr spectra in CDCl$_3$ soln.

a. The isomer from 1 was shown to have the cis-structure A by:
 1. The appearance of H$_a$ as a doublet centered at 6.6δ (upfield from H$_a$ in 2), indicating that the monsubstituted phenyl was equatorial. This conformation was also indicated by appearance of H$_c$ as a singlet at 5.7δ (downfield from H$_c$ in 2).
 2. Demonstration of a nuclear Overhauser effect between H$_b$ and H$_c$ upon double resonance, indicating a cis-diaxial relationship.

b. The isomer from 2 was shown to have the trans-structure B by:
 1. The appearance of H$_a$ as a doublet centered at 6.85δ (downfield from H$_a$ in 1), indicating that the monosubstituted phenyl was axial. This conformation was also indicated by appearance of H$_c$ as a singlet at 5.5δ (upfield from H$_c$ in 1), showing proximity of the phenyl.
 2. Absence of a nuclear Overhauser effect between H$_b$ and H$_c$.

EXAMPLE 2 cis-and trans-6-Chloro-4-(4-chlorophenyl)-1,3-benzodioxan 2-carboxylic acids a. 4',5-Dichloro-2-hydroxybenzhydrol The procedure described in example 1a was followed, using 25.0 g (93.5 mmoles) of 4',5-dichloro-2-hydroxybenzophenone[4] and 100 ml (100 mmoles) of diborane in THF solution (1M as BH$_3$). Workup gave an oil which was crystallized from 450 ml of cyclohexane to yield a colorless solid; m.p. 106°–107°. A second crop was obtained, m.p. 105°–106.5°. The total yield was 21.5 g (85%).

4. T. Houtman, Jr., U.S. Patent 2,419,553 (1947).

Anal. Calc'd. for C$_{13}$H$_{10}$Cl$_2$O$_2$: C, 58.02; H, 3.75; Cl, 26.35. Found: C, 57.70; H, 3.70; Cl, 26.26.

b. cis-and trans-6-Chloro-4-(4-chlorophenyl)-1,3-benzodioxan-2-carboxylic acids

4',5-Dichloro-2-hydroxybenzyhydrol (30.0 g, 0.116 mole) was reacted with 25.0 g (0.25-0.30 mole) of glyoxylic acid hydrate and 0.2 g of p-toluene-sulfonic acid hydrate in 600 ml of dioxane as described in Example 1b. Upon workup, 34.7 g of mixed acids was obtained (92% conversion). The mixture was dissolved hot in 300 ml of CCl$_4$ and 300 ml of alcohol-free CHCl$_3$. The solution was filtered, seeded, and stood at room temperature and then at 0°. The solid was filtered and washed with cold CCl$_4$ to give 8.5 g of almost pure cis-acid; mp 175°–178°. The mother liquor was reserved for recovery of the trans-isomer. The solid was recrystallized from CCl$_4$—CHCl$_3$ to give 4.05 g of pure cis-acid; m.p. 183°–184°. A second crop (0.94 g) was obtained; mp 182.5°–183.5°.

The first mother liquor was evaporated and the residue was dissolved in 150 ml of hot CCl$_4$ and crystallized at room temp. The solid thus obtained was filtered and recrystallized from CCl$_4$—CHCl$_3$; 5.59 g of almost pure trans-acid was obtained; m.p. 150.5°–151.5°. The mother liquor, upon standing, deposited a solid which upon recrystallization from CCl$_4$—CHCl$_3$ provided an additional 2.4 g of pure cis-acid; m.p. 180°–181.5°. The trans-isomer was recrystallized from CHCl$_3$—CCl$_4$ and again from CH$_3$NO$_2$ to give 3.05 g of pure trans-acid as a white powder; mp 159°–161°.

The yields were: cis, 17.3% (35% of available isomer); trans, 8.1% (16% of available isomer). NMR (CDCl$_3$-DMSO), δ 6.62 (d, 1H, C(5)H, cis); 5.66 (s, 1H, C(2)H, cis); 6.82 (d, 1H, C(5)H, trans); 5.44 ppm (s, 1H, C(2)H, trans).

Anal. Calc'd. for C$_{15}$H$_{10}$Cl$_2$O$_4$: C, 55.41; H, 3.10; Cl, 21.81. Found (cis): C, 55.23; H, 3.15; Cl, 22.09. Found (trans): C, 55.39; H, 3.18; Cl, 22.10.

EXAMPLE 3 cis-and trans-6-Chloro-4-(2-fluorophenyl)-1,3-benzodioxan-2-carboxylic acids a. 5-Chloro-2'-fluoro-2-hydroxybenzophenone Anhydrous AlCl$_3$ (160 g, 1.2 moles) was heated to 95° in an oil bath and 153 g (1.2 moles) of 4-chlorophenol and 190 g (1.2 moles) of 2-fluorobenzoyl chloride were added rapidly and simultaneously with stirring. Fumes were evolved and the reaction mixture liquified. After addition was completed, the mixture solidified. The bath temperature was raised to 145°; the reaction mixture again liquified and HCl was copiously evolved. The bath temperature was then raised to 195° and held for 25 minutes. The reaction mixture cooled slowly to room temperature; a glass was obtained.

The mixture was decomposed by the slow cautious addition of 6N HCl. The product was extracted out with CHCl$_3$. The combined extracts were washed well with H$_2$O, dried over anhydrous Na$_2$SO$_4$, and evaporated. The solid thus obtained was recrystallized three times from MeOH to give 209.7 g (70%) of yellowish crystals; mp 76°–80.5°.

Anal. Calc'd. for $C_{13}H_8ClFO_2$: C, 62.29; H, 3.22; Cl, 14.15. Found: C, 62.00; H, 3.40; Cl, 14.16.

b. 5-Chloro-2'-fluoro-2-hydroxybenzhydrol

Under anhydrous conditions, a stirred solution of 25.0 g (99.5 mmoles) of 5-chloro-2'-fluoro-2-hydroxybenzophenone in 250 ml of anhydrous THF was heated to reflux. The heat source was removed and 115 ml (115 mmoles) of a solution (1M in $BH_3$) of diborane in THF was added rapidly from a dropping funnel; foaming and some refluxing occurred. After addition, external heating was resumed and refluxing was continued for 5 min. A few minutes after heating was resumed, the yellow color of the ketone was discharged. The colorless solution was cooled to room temperature and worked up as described in Example 1a. An oil was obtained in quantitative yield which was used without further purification in the next step.

In one instance, crystallization of the material from cyclohexane occurred; colorless solid, mp 64°-65°. This was not reproducible.

Anal. Calc'd. for $C_{13}H_{10}ClFO_2$: C, 61.79; H, 3.99; Cl, 14.03. Found: C, 61.92; H, 3.99; Cl, 13.98.

c. cis-and trans-6-Chloro-4-(2-fluorophenyl) 1,3-benzodioxan-2-carboxylic acids

Crude 5-chloro-2'-fluoro-2-hydroxybenzhydrol (0.199 mole, assuming quantitative conversion), 38.4 g (0.379-0.416 mole) of glyoxylic acid hydrate, and 0.51 g of p-toluenesolfonic acid hydrate were reacted in 200 ml of dioxane as described in Example 1b. Distillation time was 6 hrs. and distillate volume was 3200 ml. Workup provided 38.5 g (62.5% overall conversion) of mixed acids as a reddish resin.

The mixture was dissolved in 100 ml of hot $CCl_4$, scratched, and stored at −15°. The solid (19.2 g) was filtered, washed with cold $CCl_4$, and recrystallized twice from $CH_3NO_2$ to yield 4.72 g of pure cis-acid; mp 170°-171° (bubbling), as a colorless powder. The second $CH_3NO_2$ mother liquor was evaporated and the residue was recrystallized twice from $CH_3NO_2$ to yield pure trans-acid, colorless powder, 1.71 g., mp 158°-160°.

The $CCl_4$ mother liquor was evaporated to give a second crop. This was recrystallized from $CCl_4$ and then from $CH_3NO_2$ to provide an additional 1.89 g of pure cis-acid; mp 170.5°-172° (bubbling).

The yields were: cis, 10.7% overall (34% recovery of available isomer); trans, 2.8% overall (8.9% recovery of available isomer).

NMR ($CDCl_3$-DMSO), δ6.67 (d, 1H, C(5)H, cis); 6.46 (s, 1H, C(4)H, cis); 5.66 (s, 1H, C(2)H, cis); 6.79 (d, 1H, C(5)H, trans); 6.37 (s, 1H, C(4)H, trans); 5.50 ppm (s, 1H, C(2)H, trans).

Anal. Calc'd. for $C_{15}H_{10}ClFO_4$: C, 58.36; H, 3.27; Cl, 11.49. Found (cis): C, 58.66; H, 3.49; Cl, 11.79. Found (trans): C, 58.21; H, 3.37; Cl, 11.69.

EXAMPLE 4 cis-and trans-4-Phenyl-6-nitro-1,3-benzodioxan-2-carboxylic acids a. 2-Hydroxy-5-nitrobenzophenone The literature preparation[5] of this material was inconvenient and the yields were very low. The following procedure was found to be satisfactory.

5. F. Ullman and E. Mallet, Chem. Ber., 31, 1696 (1898).

2-Chloro-5-nitrobenzophenone (50.0g, 0.191 mole) was dissolved in 500 ml of ethylene glycol at about 100°. Water (20 ml) and 16.06 g (0.286 mole) of KOH pellets were added and the mixture was stirred and heated under reflux in an oil bath at 150°-160° (internal temp., 135°) for 6 hours.

The dark solution was cooled and poured into 2 l of cold water. the mixture was made strongly basic with 40% KOH solution and stirred for a short time. The solid material was then filtered and the filter cake was washed well with $H_2O$. The filtrate was acidified with conc. HCl to give a solid material which was extracted out with $CH_2Cl_2$. The solvent was evaporated and the solid recrystallized from 95% EtOH to give 7.81 g (17%) of 2-hydroxy-5-nitrobenzophenone; mp 127°-129°.

The solid first obtained was dried and recrystallized from 95% EtOH to yield 35.6 g (65%) of 2-(2-hydroxyethoxy)-5-nitrobenzophenone; mp 124.5°-126°. Conversion to total products was thus 82%.

Anal. Calc'd. for $C_{15}H_{13}NO_5$: C, 62.71; H, 4.56; N, 4.88. Found: C, 62.51; H, 4.40; N, 4.88.

A solution of 2-(2-hydroxyethoxy)-5-nitrobenzophenone (19.08 g, 66.5 mmoles) in 475 ml of anhydrous $CH_2Cl_2$ was added all at once to a solution of 19 ml (50.2 g, 200 mmoles) of boron tribromide in 200 ml of anhydrous $CH_2Cl_2$. The solution became orange in color and some heat evolution was noted. The flask was stoppered and the reaction mixture stood at room temp for 18 hours.

The solution was poured into excess ice water; the mixture was stirred well and the layers were separated. The aqueous was extracted with two portions of $CH_2Cl_2$ and discarded. The combined organic solutions were evaporated and the solid residue was recrystallized from 95% EtOH. The yield of 2-hydroxy-5-nitrobenzophenone was 15.18 g (94%), mp 128°-129°. The total yield of product was thus 78%.

b. cis-and-trans-4-Phenyl-6-nitro-1,3-benzodioxan-2-carboxylic acids

2-Hydroxy-5-nitrobenzophenone was reduced to 2-hydroxy-5-nitrobenzhydrol essentially as described in Example 1a[6]. Following addition of the diborane, the solution was stirred and refluxed for 10 minutes. Workup gave the diol as a brown resin, still containing some THF. This material was used directly for preparation of the acid. Quantities of reactants were calculated assuming 100% yield.

6. Particular care should be exercised about halfway through the addition of the diborane - THF soln; in several experiments a sudden vigorous foaming was experienced at this point.

Crude 2-hydroxy-5-nitrobenzhydrol (0.247 mole) was condensed with 48.0 g (0.475-0.522 mole) of glyoxylic acid hydrate in 200 ml of dioxane and 0.54 g of p-toluenesolfonic acid hydrate as described in Example 1b. Distillation time was 3 hours and 1880 ml of distillate was collected. The usual workup was performed. During filtration of the ether solution of mixed acids from the $MgSO_4$ dessicant, a solid suddenly separated. Repeated washings with $CH_2Cl_2$ cleared the solid from both the filter and the filtrate. The filtrate was evaporated to yield a dark resin which was dissolved in 500 ml of ether. The solution was seeded; immediate separation of a crystalline solid began. The mixture was allowed to crystallize at room temperature and was then stored at 0°.

Filtration, washing with 50 ml of cold (−15°) ether, and drying (110°, briefly) gave 16.9 g of pure cis-acid as light yellowish needles; mp 193°–195°. The mother liquor was evaporated to 100 ml, seeded, and stored at −15°, impure trans-acid (12.1 g) was obtained. This was recrystallized from 130 ml of $CH_3NO_2$ to give 7.86 g of pure trans-acid; mp 188.5°–190°. The yields were: cis, 22.8% (45% of available isomer; trans, 10.6% (21.2% of available isomer).

Nmr ($CDCl_3$-DMSO), $\delta$7.51 (d, 1H, C(5)H, cis); 5.77 (s, 1H, C(2)H, cis); 7.75 (d, 1H, C(5)H, trans); 5.58 ppm (s, 1H, C(2)H, trans).

Anal. Calc'd. for $C_{15}H_{11}NO_6$: C, 59.80; H, 3.68; N, 4.65. Found (cis): C, 59.70; H, 3.84; N, 4.65. Found (trans): C, 59.70; H, 3.61; N, 4.63.

EXAMPLE 5 cis-6-Chloro-2-methylaminomethyl-4-phenyl-1,3-benzodioxan hydrochloride. BL-3186 a. cis-6-Chloro-N-methyl-4-phenyl-1,3-benzodioxan-2-carboxamide

To a stirred slurry, under nitrogen, of 8.2 g (28.1 mmoles) of cis-6-chloro-4-phenyl-1,3-benzodioxan-2-carboxylic acid in 300 ml of anhydrous benzene was added slowly 33g (280 mmoles) of thionyl chloride. A few drops of anhydrous DMF (dimethylformamide) was added and the mixture was stirred under reflux for 3 hours.

Solution was attained at the boil. The solvent and excess $SOCl_2$ were removed under reduced pressure; the residue was flashed down with two portions of benzene to remove traces of $SOCl_2$.

The solid acid chloride was dissolved in $CH_2Cl_2$ and the solution was saturated with anhydrous $CH_3NH_2$. A copious precipitate was observed. The mixture was stirred for 15 minutes, saturated again with $CH_3NH_2$, stirred for 1 hour, saturated a third time with $CH_3NH_2$, and finally stirred overnight at room temperature.

The mixture was washed with water (four portions), saturated $NaHCO_3$ solution (two portions), and saturated brine (one portion) and dried over anhydrous $Na_2SO_4$. The solvent was evaporated and the residual solid was recrystallized from absolute ethanol to give 5.97 g of colorless crystals; mp 169°–170°. A second crop was obtained to raise the yield to 7.67 g (90%).

Anal. Calc'd. for $C_{16}H_{14}ClNO$: C, 63.27; H, H, 4.64; N, 4.61; Cl, 11.67. Found: C, 63.30; H, 4.72; N, 4.63; Cl, 11.27.

b. cis-6-Chloro-2-methylaminomethyl-4-phenyl-1,3-benzodioxan hydrochloride

To a stirred solution, under nitrogen, of 8.0 g (26.4 mmoles) of cis-6-chloro-N-methyl-4-phenyl-1,3-benzodioxan-2-carboxamide was added dropwise, at room temperature, 150 ml (150 mmoles) of diborane (1M as $BH_3$) in THF solution. After addition was complete, the solution was stirred and refluxed for 21 hours.

The solution was cooled in an ice bath the 125 ml of 5% HCL was added dropwise over a period of 1 hour. The solution was then evaporated under reduced pressure. The residue was partitioned between ether and dil. NaOH solution. The layers were separated and the alkaline aqueous solution was extracted with ether. The extracts were combined and washed with saturated $NaHCO_3$ solution, water and saturated brine and dried over anhydrous $K_2CO_3$.

The solution was concentrated and the salt was formed with HCl gas. The mixture was evaporated and the residual solid was dissolved in hot absolute EtOH. The solution was filtered, reheated, and ether was added to cloudiness at the boil. The product crystallized at room temp to give 6.52 g of colorless solid; mp 242.5°–243°. The mother liquor was evaporated and the residue was recrystallized in a like manner to yield a second crop, 2.25 g; mp 239°–240°.

The total yield was 98%. Anal. Calc'd. for $C_{16}H_{16}ClNO_2 \cdot HCl$: C, 58.91; H, 5.25; N, 4.29. Found: C, 58.94; H, 5.34; N, 4.09.

EXAMPLE 6 cis-6-Chloro-4-phenyl-2-(2-propylaminomethyl)-1,3-benzodioxan hydrochloride. BL-3396 a. cis-6-Chloro-4-phenyl-N-(2-propyl)-1,3-benzodioxan-2-carboxamide

To a solution at room temperature of 6.0 g (20.6 mmoles) of cis-6-chloro-4-phenyl-1,3-benzodioxan-2-carboxylic acid and ca. 1 ml of anhydrous DMF (dimethylformamide) in 300 ml of anhydrous $CH_2Cl_2$ was added dropwise a solution of 8.95 ml (123.6 mmoles) of thionyl chloride in 50 ml of anhydrous $CH_2Cl_2$. After addition, the solution was stirred and refluxed for 2.5 hours. The solvent and excess $SOCl_2$ were then removed under reduced pressure and the residue was flashed down twice with anhydrous benzene to remove traces of $SOCl_2$. The residue was redissolved in ca. 200 ml of $CH_2Cl_2$ and a solution of 7.7 g (130 mmoles) of 2-aminopropane in ca. 50 ml of $CH_2Cl_2$ was added. Heat was evolved. The solution was mixed well and allowed to stand in a stoppered flask at room temperature for 65 hours.

The solution was washed with 5% HCl solution (four portions), water (two portions), and saturated brine (two portions) and was dried over anhydrous $Na_2SO_4$. The solvent was evaporated to yield 4.5 g (99%) of amide. A sample was recrystallized from abs EtOH, mp 185°–186°.

Anal. Calc'd. for $C_{18}H_{18}NO_3Cl$: C, 65.15; H, 5.47; N, 4.22. Found: C, 65.02; H, 5.50; N, 4.29.

b. cis-6-Chloro-4-phenyl-2-(2-propylaminomethyl)-1,3-benzodioxan hydrochloride

A solution of cis-6-chloro-4-phenyl-N-(2-propyl)-1,3-benzodioxan-2-carboxamide (6.6 g, 20.0 mmoles) in 400 ml of anhydrous THF was treated with 80 ml (80 mmoles) of diborane in THF solution (1M as $BH_3$) and the reaction mixture was worked up essentially as described in Example 5b. The oily amine was converted to the hydrochloride in anhydrous ether; 7.4 g of colorless powder was obtained. Recrystallization from absolute EtOH gave 5.96 g (84%) of colorless crystals; mp 224.5°–225.5°.

Anal. Calc'd. for $C_{18}H_{20}NO_2 \cdot HCl$: C, 61.02; H, 5.98; N, 3.95. Found: C, 61.20; H, 6.09; N, 4.05.

EXAMPLE 7 trans-6-Chloro-4-(2-fluorophenyl)-2-(2-propylaminomethyl)-1,3-benzodioxan hydrochloride. BL-3681A a. trans-6-Chloro-4-(2-fluorophenyl)-N-(2-propyl)-1,3-benzodioxan-2-carboxamide A solution of 3.38 g (10.9 mmoles) of trans-6-chloro-4-(2-fluorophenyl)-1,3-benzodioxan-2-carboxylic acid, 10.0 ml (16.4 g, 137 mmoles) of thionyl chloride, and 5 drops of anhydrous DMF in 200 ml of anhydrous $Ch_2Cl_2$ was refluxed for 2 hours; the solvent and excess $SOCl_2$ were removed under reduced pressure and the residue was flashed down with 3 portions of anhydrous benzene to remove traces of $SOCl_2$. The acid chloride was redissolved in 100 ml of anhydrous $CH_2Cl_2$ and 5.57 ml (3.86 g, 65.4 mmoles) of 2-aminopropane was added all at once; heat was evolved. The reaction mixture stood in a stoppered flask for 16 hours.

The reaction mixture was evaporated. The residue was partitioned between ether and water and the mixture was worked up as described in Example 6a. The solid amide obtained was recrystallized from EtOH—$H_2O$ to give 3.40 g (89%) of colorless needles; mp 125°–126°.

Anal. Calc'd. for $C_{18}H_{17}ClFNO_3$: C, 61.80; H, 4.90; N, 4.01; Cl, 10.14. Found: C, 61.83; H, 5.20; N, 4.05; Cl, 10.30.

b. trans-6-Chloro-4-(2-fluorophenyl-2-(2-propylaminomethyl-1,3-benzodioxan hydrochloride The reduction was performed essentially as described in Example 5b, employing 2.86 g (8.18 mmoles) of trans-6-chloro-4-(2-fluorophenyl)-N-(2-propyl)-1,3-benzodioxan-2-carboxamide in 100 ml of anhydrous THF and 49 ml (49mmoles) of 1M (as $BH_3$) diborane in THF solution. The reaction mixture was hydrolyzed with 6N HCl and worked up as described previously. The hydrochloride salt of the amine was formed in anhydrous ether; crystallization was slow and the mixture was stored at 0° until separation was complete. The colorless crystals (2.54 g, 84% yield, mp 216°–218° (dec)), were recrystallized from acetone. Recovery was 88% (2.23 g, mp 214.5°–216° (dec)).

Anal. Calc'd. for $C_{18}H_{19}ClFNO_2.HCl$: C, 58.07 H, 5.42; N, 3.76; Cl, 19.05. Found: C, 58.12; H, 5.55; N, 3,79; Cl, 18.87.

EXAMPLE 8 trans-4-(2-Fluorophenyl)-2-(2-propylaminomethyl)-1,3-benzodioxan hydrochloride

To a solution of 1.06 g (2.84 mmoles) of trans-6-chloro-4-(2-fluorophenyl)-2-(2-propylaminomethyl)-1,3-benzodioxan hydrochloride in 200 ml of EtOH was added 0.79 ml (0.56 g, 5.68 mmoles) of triethylamine and 0.51 g of 10% Pd on carbon catalyst; the mixture was hydrogenated at an initial gauge pressure of 3 atm. Hydrogen uptake was initially rapid but slowed after ca. 10 min. After 2 hours, it was complete. The catalyst was filtered, the solvent was evaporated, and the residue was partitioned between ether and dil. $NaHCO_3$ solution. The ether solution was washed with two portions of water, dried and evaporated.

The hydrochloride salt of the amine was formed in anhydrous ether. Crystallization from ether was slow. The salt was filtered and recrystallized from acetone; colorless cyrstals, 0.715 g (74% yield); mp 182°–183.5°.

Anal. Calc'd. for $C_{18}H_{20}FNO_2.HCl$: C, 63.99; H, 6.27; N, 4.15; Cl, 10.50. Found: C, 63.87; H, 6.06; N, 3.98; Cl, 10.55.

EXAMPLE 9

General procedure for the preparation of compounds of the generic formula IV having the structure

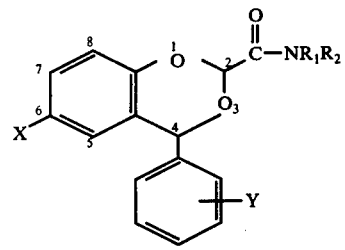

Substitution in the procedure of examples 5a, 6a or 7a for the amine used therein of an equimolar amount of the appropriate amine produced the compounds indicated in Table Ia and Ib below:

Table Ia.

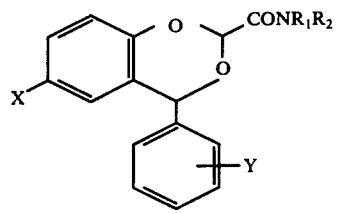

| Cmpd. No. | X | Y | $NR_1R_2$ | cis or trans | m.p. °C | Recrystallization Solvent* |
|---|---|---|---|---|---|---|
| 1 | Cl | H | $NH_2$ | cis | 190.5–191.5 | F |
| 2 | Cl | H | $NH_2$ | trans | 201–202.5 | K |
| 3 | Cl | 4-Cl | $NH_2$ | cis | 199–200 | F |
| 4 | Cl | 2-F | $NH_2$ | cis | 205–205.5 | A,E |
| 5 | $NO_2$ | H | $NH_2$ | cis | 205–206 | A,E |
| 6 | Cl | H | NHMe | cis | 169–170 | F |
| 7 | Cl | H | NHMe | trans | 177.5–179 | K,L |
| 8 | Cl | 4-Cl | NHMe | cis | 195–196.5 | F |
| 9 | Cl | 2-F | NHMe | cis | 184.5–186.5 | B,E |
| 10 | $NO_2$ | H | NHMe | cis | 190–191 | A |
| 11 | Cl | H | NHEt | cis | 162–163 | F |
| 12 | Cl | H | NHEt | trans | 128–129 | A,E |
| 13 | Cl | H | NH-n-Pr | cis | 136–137 | F |

Table Ia.-continued

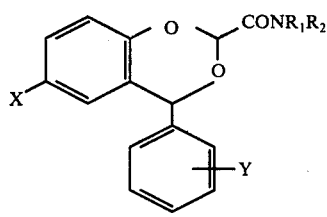

| Cmpd. No. | X | Y | NR₁R₂ | cis or trans | m.p. °C | Recrystallization Solvent* |
|---|---|---|---|---|---|---|
| 14 | Cl | H | NH-n-Pr | trans | 109–110.5 | A,E |
| 15 | Cl | H | NH-iso-Pr | cis | 185–186 | F |
| 16 | Cl | H | NH-iso-Pr | trans | 133.5–135 | A,E |
| 17 | Cl | 4-Cl | NH-iso-Pr | cis | 217–218 | F |
| 18 | Cl | 2-F | NH-iso-Pr | cis | 165–166 174–175.5 | B B,E |
| 19 | Cl | 2-F | NH-iso-Pr | trans | 125–126 | A,E |
| 20 | NO₂ | H | NH-iso-Pr | cis | 182.5–183.5 | A,E |
| 21 | Cl | H | NH—◁ | cis | 207.5–208 | F |
| 22 | Cl | H | NH—◁ | trans | 174.5–177.5 | A |
| 23 | Cl | H | NH-iso-Bu | cis | 157–158 | F |
| 24 | Cl | H | NH-sec-Bu | cis | 190–191 | F |
| 25 | Cl | H | NH-t-Bu | cis | 174.5–175.5 | F |
| 26 | Cl | H | NH—□ | cis | 194.5–195.5 | F |
| 27 | Cl | H | NH—⬠ | cis | 181–183 | F |
| 28 | Cl | H | NH—⬡ | cis | 192–193.5 | F |
| 29 | Cl | H | NMe₂ | cis | 220–221 | F |
| 30 | Cl | H | NMe₂ | trans | — | — |
| 31 | Cl | 2-F | NMe₂ | cis | 192–194 | A,E |
| 32 | NO₂ | H | NMe₂ | cis | 169–170 | A,E |
| 33 | Cl | H | NEt₂ | cis | 188.5–190 | F |
| 34 | Cl | H | NEt₂ | trans | 82–85 | B,E |
| 35 | Cl | H | N-pyrrolidinyl | cis | 234.5–235 | F |
| 36 | Cl | H | N-pyrrolidinyl | trans | 137–138.5 | B,E |
| 37 | Cl | H | N-piperidinyl | cis | 174–175.5 | F |
| 38 | Cl | H | N-morpholinyl | cis | 174–175 | F |
| 39 | Cl | N-morpholinyl | | trans | 174.5–177.5 | M |
| 40 | Cl | H | N-(4-Me-piperazinyl) | cis | 173–174.5 | F |
| 41 | Cl | H | N-(1,4-dioxa-8-azaspiro) | cis | 216–217.5 | F |

*A, 95% EtOH; B, MeOH; C, acetone; D, ether; E, water; F, absolute EtOH; G, Skellysolve B (essentially n-hexane), H, acetonitrile; I, isopropyl alcohol; K, CHCl₃; L, CCl₄; M, nitromethane.

Table Ib.

| Cmpd. No. | Calcd | | | Found | | |
|---|---|---|---|---|---|---|
| | C | H | N | C | H | N |
| 1 | 62.18 | 4.18 | 4.84 | 61.84 | 4.21 | 4.90 |
| 2 | 62.19 | 4.18 | 4.83 | 61.99 | 4.43 | 4.86 |
| 3 | 55.57 | 3.42 | 4.32 | 55.30 | 3.52 | 4.34 |
| 4 | 58.55 | 3.60 | 4.55 | 58.58 | 3.64 | 4.65 |

Table Ib.-continued

| Cmpd. No. | Calcd C | Calcd H | Calcd N | Found C | Found H | Found N |
|---|---|---|---|---|---|---|
| 5 | 60.00 | 4.03 | 9.33 | 59.93 | 4.14 | 9.39 |
| 6 | 63.27 | 4.64 | 4.61 | 63.30 | 4.72 | 4.63 |
| 7 | 63.27 | 4.64 | 4.61 | 63.16 | 4.64 | 4.56 |
| 8 | 56.83 | 3.87 | 4.14 | 56.80 | 4.03 | 4.25 |
| 9 | 59.73 | 4.07 | 4.35 | 59.73 | 4.26 | 4.44 |
| 10 | 61.14 | 4.49 | 8.91 | 61.14 | 4.53 | 8.76 |
| 11 | 64.25 | 5.06 | 4.41 | 63.81 | 5.19 | 4.33 |
| 12 | 64.25 | 5.07 | 4.41 | 64.49 | 5.19 | 4.37 |
| 13 | 65.16 | 5.47 | 4.22 | 64.84 | 5.53 | 4.24 |
| 14 | 65.16 | 5.47 | 4.22 | 64.82 | 5.67 | 4.19 |
| 15 | 65.16 | 5.47 | 4.22 | 65.02 | 5.50 | 4.29 |
| 16 | 65.16 | 5.47 | 4.22 | 65.12 | 5.66 | 4.25 |
| 17 | 59.03 | 4.68 | 3.82 | 59.29 | 4.88 | 3.98 |
| 18 | 61.80 | 4.90 | 4.01 | 61.91 | 5.13 | 4.06 |
| 19 | 61.80 | 4.90 | 4.01 | 61.83 | 5.20 | 4.05 |
| 20 | 63.15 | 5.30 | 8.18 | 62.99 | 5.48 | 8.23 |
| 21 | 65.55 | 4.89 | 4.25 | 65.34 | 5.02 | 4.25 |
| 22 | 65.55 | 4.89 | 4.25 | 65.12 | 5.04 | 4.27 |
| 23 | 65.98 | 5.83 | 4.05 | 65.60 | 5.86 | 4.09 |
| 24 | 65.98 | 5.83 | 4.05 | 65.76 | 5.70 | 4.02 |
| 25 | 65.98 | 5.83 | 4.05 | 65.69 | 5.83 | 3.79 |
| 26 | 66.37 | 5.28 | 4.08 | 66.42 | 5.38 | 3.99 |
| 27 | 67.13 | 5.63 | 3.92 | 66.95 | 5.70 | 3.96 |
| 28 | 67.82 | 5.96 | 3.77 | 67.77 | 5.96 | 3.63 |
| 29 | 65.07 | 5.14 | 4.46 | 65.11 | 4.99 | 4.98 |
| 30 | 64.26 | 5.08 | 4.41 | 64.11 | 5.05 | 4.48 |
| 31 | 60.81 | 4.50 | 4.17 | 60.94 | 4.53 | 4.20 |
| 32 | 62.19 | 4.91 | 8.53 | 61.97 | 5.07 | 8.42 |
| 33 | 65.98 | 5.83 | 4.05 | 65.73 | 5.95 | 3.77 |
| 34 | 65.98 | 5.83 | 4.05 | 65.87 | 5.89 | 3.87 |
| 35 | 66.37 | 5.28 | 4.08 | 66.37 | 5.27 | 4.04 |
| 36 | 66.37 | 5.28 | 4.08 | 66.45 | 5.39 | 3.86 |
| 37 | 67.13 | 5.63 | 3.92 | 67.27 | 5.66 | 3.91 |
| 38 | 63.42 | 5.04 | 3.89 | 63.12 | 5.15 | 3.96 |
| 39 | 63.42 | 5.04 | 3.89 | 63.48 | 5.24 | 4.09 |
| 40 | 64.42 | 5.68 | 7.52 | 64.57 | 5.58 | 7.34 |
| 41 | 63.53 | 5.33 | 3.37 | 63.45 | 5.29 | 3.36 |

EXAMPLE 10

General procedure for the preparation of compounds of the generic formula IV having the structure

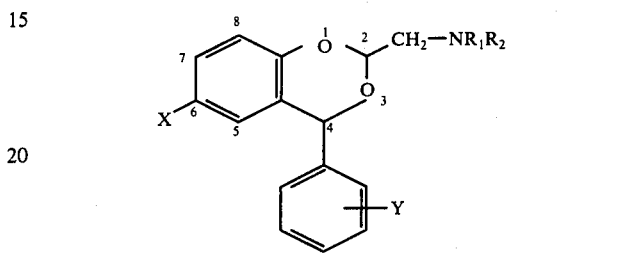

Substitution in the procedure of examples 5b, 6b or 7b for the amine used therein of an equimolar amount of the appropriate amine produced the compounds indicated in Tables IIa and IIb below:

Table IIa

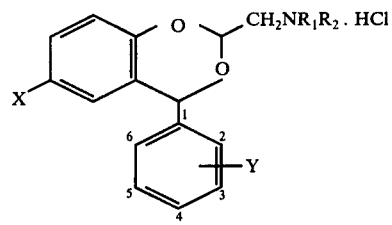

| Cmpd. No. | X | Y | NR₁R₂ | cis or trans | m.p. °C | Recrystallization Solvent* |
|---|---|---|---|---|---|---|
| 1B | Cl | H | NH₂ | cis | 203-204.5 | B,D |
| 2B | Cl | H | NH₂ | trans | 212.5-213.5 (dec) | D |
| 3B | H | H | NH₂ | cis | 215-218.5 228.5-230 | F,G F |
| 4B | H | H | NH₂ | trans | 182.5-183 (dec) | C |
| 5B | Cl | 4-Cl | NH₂ | cis | 254-256 | F,G |
| 6B | Cl | 2-F | NH₂ | cis | 219-219.5 (dec) | C |
| 7B | NO₂ | H | NH₂ | cis | 197-198 (dec) | B,D |
| 8B | Cl | H | NHMe | cis | 242.5-243 | D,F |
| 9B | Cl | H | NHMe | trans | 234.5-235 (dec) | B,D |
| 10B | H | H | NHMe | cis | 226.5-227 | D,F |
| 11B | H | H | NHMe | trans | 185-187.5 | B,D |
| 12B | Cl | 4-Cl | NHMe | cis | 241.5-242.5 | F |
| 13B | Cl | 2-F | NHMe | cis | 247-248 (dec) | B,D |
| 14B | NO₂ | H | NHMe | cis | 249-250 (dec) | B,D |
| 15B | Cl | H | NHEt | cis | 234-235 | F |
| 16B | Cl | H | NHEt | trans | 249-250 (dec) | B |
| 17B | H | H | NHEt | cis | 214-215.5 | F |
| 18B | H | H | NHEt | trans | 217-217.5 (dec) | B,D |
| 19B | Cl | H | NH-n-Pr | cis | 227-228 (dec) | F,G |
| 20B | Cl | H | NH-n-Pr | trans | 237-239 (dec) | B,D |
| 21B | H | H | NH-n-Pr | trans | 178-179.5 | C |
| 22B | Cl | H | NH-iso-Pr | cis | 226-227 | F |
| 23B | Cl | H | NH-iso-Pr | trans | 230-231 (dec) | B,D |
| 24B | H | H | NH-iso-Pr | cis | 203.5-204 | C |
| 25B | H | H | NH-iso-Pr | trans | 200.5-201 | C |

Table IIa-continued

Structure: benzene ring with O-CH(CH₂NR₁R₂·HCl)-O bridge forming a dioxane ring, attached at C1 to a second phenyl ring bearing Y substituent (positions 2–6); X substituent on first ring.

| Cmpd. No. | X | Y | NR₁R₂ | cis or trans | m.p. °C | Recrystallization Solvent* |
|---|---|---|---|---|---|---|
| 26B | Cl | 4-Cl | NH-iso-Pr | cis | 234–235 (dec) | F,D |
| 27B | Cl | 2-F | NH-iso-Pr | cis | 203–204 | C |
| 28B | Cl | 2-F | NH-iso-Pr | trans | 214.5–216 (dec) | C |
| 29B | H | 2-F | NH-iso-Pr | trans | 182–183.5 | C |
| 30B | NO₂ | H | NH-iso-Pr | cis | 172–174.5 (dec) | H |
| 31B | Cl | H | NH-cyclopropyl | cis | 210–211 | F |
| 32B | Cl | H | NH-cyclopropyl | trans | 222–226.5 (dec) | B |
| 33B | H | H | NH-cyclopropyl | trans | 205–206 (dec) | B,D |
| 34B | Cl | H | NH-iso-Bu | cis | 166–167.5 | F,D |
| 35B | Cl | H | NH-sec-Bu | cis | 205–206 | C |
| 36B | Cl | H | NH-t-Bu | cis | 219–219.5 | H |
| 37B | Cl | H | NHCH₂-cyclopropyl | cis | 176–177 | F |
| 38B | Cl | H | NH-cyclobutyl | cis | 242–243.5 | F |
| 39B | Cl | H | NH-cyclopentyl | cis | 220–221.5 | — |
| 40B | Cl | H | NH-cyclohexyl | cis | 185.187.5 | F,D |
| 41B | Cl | H | NMe₂ | cis | 217.5–219 | B,D |
| 42B | Cl | H | NMe₂ | trans | 167.5–169.5 | H,D |
| 43B | Cl | 4-Cl | NMe₂ | cis | 233–234 | H |
| 44B | Cl | 2-F | NMe₂ | cis | 192–194 | C |
| 45B | Cl | H | O↑NMeEt | cis | 158–160 | F |
| 46B | Cl | H | NMeEt | trans | 144–147.5 | C |
| 47B | Cl | H | NEt₂ | cis | 143.5–145 | F,G |
| 48B | Cl | H | NEt₂ | trans | foam 95–125 | B,D |
| 49B | Cl | H | pyrrolidinyl | cis | 169–171 | F,D |
| 50B | Cl | H | pyrrolidinyl | trans | 241.5–242 (dec) | B,D |
| 51B | Cl | H | piperidinyl | cis | 234.5–235 | F,G |
| 52B | H | H | piperidinyl | cis | 290.5–210.5 | F,G |
| 53B | Cl | H | morpholinyl | cis | 210–212.5 | F,D |

Table IIa-continued

| Cmpd. No. | X | Y | NR₁R₂ | cis or trans | m.p. °C | Recrystallization Solvent* |
|---|---|---|---|---|---|---|
| 54B | Cl | H | N(piperazine)N—CH₃ . HCl | cis | 207–209 | F |
| 55B | Cl | H | N(piperidine-spiro-dioxolane) | cis | 219–220 | I |

*A, 95% EtOH; B, MeOH; C, acetone; D, ether; E, water; F, absolute EtOH; G, Skellysolve B; (essentially n-hexane) H, acetonitrile; I, isopropyl alcohol; K, CHCl₃; L, CCl₄; M, nitromethane.

Table IIb.

| Cmpd. No. | Calcd C | Calcd H | Calcd N | Found C | Found H | Found N |
|---|---|---|---|---|---|---|
| 1B | 57.71 | 4.84 | 4.49 | 57.60 | 4.94 | 4.31 |
| 2B | 57.71 | 4.84 | 4.49 | 57.77 | 4.87 | 4.51 |
| 3B | 64.86 | 5.80 | 5.04 | 64.86 | 5.74 | 5.03 |
| 4B | 64.86 | 5.81 | 5.04 | 65.06 | 5.90 | 5.06 |
| 5B | 51.97 | 3.96 | 3.93 | 51.87 | 4.05 | 4.00 |
| 6B | 54.56 | 4.27 | 4.24 | 54.25 | 4.20 | 4.17 |
| 7B | 55.82 | 4.68 | 8.68 | 56.05 | 4.92 | 8.77 |
| 8B | 58.91 | 5.25 | 4.29 | 58.94 | 5.34 | 4.09 |
| 9B | 58.91 | 5.25 | 4.29 | 59.06 | 5.16 | 4.44 |
| 10B | 65.86 | 6.22 | 4.80 | 65.79 | 6.20 | 4.56 |
| 11B | 65.86 | 6.22 | 4.80 | 66.06 | 6.03 | 4.69 |
| 12B | 53.28 | 4.47 | 3.88 | 53.37 | 4.60 | 3.77 |
| 13B | 55.83 | 4.69 | 4.07 | 56.01 | 4.90 | 4.08 |
| 14B | 57.06 | 5.09 | 8.32 | 57.23 | 5.28 | 8.35 |
| 15B | 60.01 | 5.63 | 4.12 | 60.10 | 5.86 | 3.94 |
| 16B | 60.01 | 5.63 | 4.12 | 59.87 | 5.68 | 4.27 |
| 17B | 66.76 | 6.59 | 4.58 | 66.46 | 6.73 | 4.60 |
| 18B | 66.77 | 6.59 | 4.58 | 66.55 | 6.65 | 4.42 |
| 19B | 61.02 | 5.98 | 3.95 | 60.81 | 5.92 | 4.00 |
| 20B | 61.02 | 5.98 | 3.95 | 60.88 | 6.01 | 3.75 |
| 21B | 67.59 | 6.93 | 4.38 | 67.52 | 6.94 | 4.39 |
| 22B | 61.02 | 5.98 | 3.95 | 60.97 | 6.08 | 4.00 |
| 23B | 61.02 | 5.98 | 3.95 | 60.68 | 6.01 | 3.90 |
| 24B | 67.59 | 6.93 | 4.38 | 67.26 | 6.96 | 4.40 |
| 25B | 67.59 | 6.93 | 4.38 | 67.70 | 6.92 | 4.33 |
| 26B | 55.62 | 5.19 | 3.60 | 55.83 | 5.35 | 3.64 |
| 27B | 58.07 | 5.42 | 3.76 | 58.23 | 5.59 | 3.73 |
| 28B | 58.07 | 5.42 | 3.76 | 58.12 | 5.55 | 3.79 |
| 29B | 63.99 | 6.27 | 4.15 | 63.87 | 6.06 | 3.98 |
| 30B | 59.25 | 5.80 | 7.68 | 59.16 | 6.04 | 7.77 |
| 31B | 61.37 | 5.43 | 3.98 | 60.99 | 5.43 | 3.92 |
| 32B | 61.37 | 5.44 | 3.98 | 61.40 | 5.40 | 3.89 |
| 33B | 68.02 | 6.34 | 4.41 | 67.76 | 6.46 | 4.18 |
| 34B | 61.96 | 6.29 | 3.80 | 61.62 | 6.27 | 3.72 |
| 35B | 61.96 | 6.29 | 3.80 | 61.87 | 6.30 | 3.77 |
| 36B | 61.96 | 6.29 | 3.80 | 61.80 | 6.35 | 3.86 |
| 37B | 66.37 | 5.28 | 4.08 | 66.19 | 5.36 | 4.15 |
| 38B | 62.30 | 5.78 | 3.82 | 62.45 | 5.79 | 4.11 |
| 39B | 63.15 | 6.10 | 3.68 | 63.21 | 6.10 | 3.52 |
| 40B | 63.96 | 6.39 | 3.55 | 63.74 | 6.34 | 3.51 |
| 41B | 60.01 | 5.63 | 4.12 | 60.06 | 5.75 | 4.15 |
| 42B | 60.01 | 5.63 | 4.12 | 60.07 | 5.63 | 4.21 |
| 43B | 54.49 | 4.84 | 3.74 | 54.20 | 4.84 | 3.92 |
| 44B | 56.99 | 5.06 | 3.91 | 56.88 | 5.12 | 3.85 |
| 45B | 58.11 | 5.72 | 3.78 | 57.98 | 5.66 | 3.62 |
| 46B | 61.02 | 5.98 | 3.95 | 60.89 | 5.98 | 3.92 |
| 47B | 61.96 | 6.29 | 3.80 | 62.14 | 6.16 | 4.01 |
| 48B | 61.96 | 6.29 | 3.80 | 62.11 | 6.33 | 3.66 |
| 49B | 62.30 | 5.78 | 3.83 | 62.39 | 6.12 | 3.57 |
| 50B | 62.30 | 5.78 | 3.83 | 62.36 | 5.85 | 3.84 |
| 51B | 63.14 | 6.09 | 3.68 | 62.86 | 6.17 | 3.43 |
| 52B | 69.45 | 6.99 | 4.05 | 69.27 | 7.11 | 4.05 |
| 53B | 59.69 | 5.54 | 3.66 | 59.41 | 5.53 | 3.58 |
| 54B | 55.63 | 5.84 | 6.49 | 55.94 | 5.71 | 6.48 |
| 55B | 60.28 | 5.75 | 3.20 | 60.03 | 5.82 | 3.32 |

All temperatures reported herein are in degrees centigrade (° C).

EXAMPLE 11

A.

trans-6-Chloro-4-phenyl-N-(3-dimethylaminopropyl)-1,3-benzodioxan-2-carboxamide hydrochloride (BL-4932A)

trans-6-Chloro-4-phenyl-1,3-benzodioxan-2-carboxylic acid (2.91 g., 10 mmoles), thionyl chloride (10 ml) and dry DMF (3drops) were added to dry $CH_2Cl_2$ (100 ml) and heated at reflux for 2 hrs. The solvent and excess thionyl chloride were removed under reduced pressure with the aid of added benzene. The remaining oily acid chloride was redissolved in dry $CH_2Cl_2$ (50 ml) and dimethylaminopropyl amine (1.02 g., 10 mmoles) was added with stirring (exothermic). Stirring at 22° under an atmosphere of dry $N_2$ was carried out for 22½ hrs, followed by refluxing for 30 mins. Solvent removal afforded a foam which was triturated with $Et_2O$/EtOAc to give a white solid. Recrystallization from isopropyl alcohol gave white crystals (2.55 g., 62.1%, mp 188°–191.5° d). Spectra (ir, nmr) were consistent with the structure; mass spec M += 375.

Anal. calc'd. for $C_{20}H_{23}ClN_2O_3 \cdot HCl$: C, 58.40; H, 5.88; N, 6.81.

(Corrected for 2.4% $H_2O$) Found: C, 58.38; H, 5,91; N, 7.61.

B.

trans-6-chloro-4-phenyl-2-[N-(3-dimethylaminopropyl)aminomethyl]-1,3-benzodioxan hydrochloride Substitution in the procedure of example 5b for the cis-6-chloro-N-methyl-4-phenyl-1,3-benzodioxan-2-carboxamide used therein of an equimolar quantity of BL-4932A produces the title compound.

EXAMPLE 12

A.

trans-4-Phenyl-N-(3-dimethylaminopropyl)-1,3-benzodioxan-2-carboxamide hydrochloride (BL-5028A)

trans-6-Chloro-4-phenyl-N-(3-dimethylaminopropyl)1,3-benzodioxan-2-carboxamide hydrochloride (1.0 g., 2.43 mmole) was mixed with triethylamine (0.526 g., 5.2 mmole) and 30% Pd on Celite catalyst (0.3 g.,) in 200 ml of absolute EtOH and hydrogenated in a Parr apparatus for 30 mins. at an initial $H_2$ pressure of 48 psi. The uptake was 13 lbs. of $H_2$ and after catalyst removal, the filtrate was stripped of solvent under reduced pressure. The residue was partitioned between $CH_2Cl_2$ and 2% $Na_2CO_3$ solution. After extraction of the aqueous with a second portion of $CH_2Cl_2$, the organics were combined, washed with $H_2O$, dried $(MgSO_4)$ and stripped to a syrup under reduced pressure. The .HCL salt was formed in $CH_2Cl_2$ in the usual manner, and after solvent removal, crystallization was effected by trituration in hot EtOAc, followed by cooling (0.66 g., 72%). Recrystallization from EtOAc-abs EtOH gave analytical material (mp 165°–170° d).

Anal. calc'd. for $C_{20}H_{24}N_2O_3.HCl$: C, 63.74 H. 6.69; N, 7.43; Cl, 9.41.
Found: C, 64.09; H, 6.71; N, 7.32; Cl, 9.62.

B.
trans-4-Phenyl-2-[N-(3-dimethylaminopropyl)-aminomethyl]-1,3-benzodioxan hydrochloride Substitution in the procedure of example 5b for the cis-6-chloro-N-methyl-4-phenyl-1,3-benzodioxan-2-carboxamide used therein of an equimolar quantity of BL-5028A produces the title compound.

EXAMPLE 13

A.
cis-6-Chloro-4-phenyl-N-(3-dimethylaminopropyl)1,3-benzodioxan-2-carboxamide hydrochloride
(BL-4971A)

cis-6-Chloro-4-phenyl-1,3-benzodioxan-2-carboxylic acid (2.91 g., 10 mmoles), ethionyl chloride (10 ml) and dry DMF (4 drops) were refluxed in 100 ml of dry $CH_2Cl_2$ for 2 hrs. Removal of solvent and excess reagent under reduced pressure afforded the crude acid chloride which was then redissolved in $CH_2Cl_2$ (50 ml) and treated with dimethylaminopropyl amine (1.53 g., 15 mmloes). The reaction was somewhat exothermic and the stirred mixture was maintained at 20° for 35 mins., and then at reflux for 45 mins. After solvent removal, the residue was partitioned between 5% $Na_2CO_3$ solution and $CH_2Cl_2$ (2 portions). The organics were then washed with brine, dried $(MgSO_4)$ and treated with HClg. Solvent removal and crystallization of the residue from isopropyl alcohol gave the product as a white solid (3.34 g., 81.3%). Recrystallization from abs EtOH-:$Et_2O$ afforded pure material (mp 213°–216° d).

Anal. calc'd. for $C_{20}H_{23}ClN_2O_3.HCl$: C, 58.40; H, 5.88; N, 6.81.
Found: C, 58.83; H, 5.85; N, 6.81.

B.
cis-6-Chloro-4-phenyl-2-[N-(3-dimethylaminopropyl)aminomethyl]-1,3-benzodioxan hydrochloride Substitution in the procedure of example 5b for the cis-6-chloro-N-methyl-4-phenyl-1,3-benzodioxan-2-carboxamide used therein of an equimolar quantity of BL-4971A produces the title compound.

EXAMPLE 14

A.
cis-4-Phenyl-N-(3-dimethylaminopropyl)-1,3-benzodioxan-2-carboxamide hydrochloride (BL-4981A)

cis-6-Chloro-4-phenyl-N-(3-dimethylaminopropyl)-1,3-benzodioxan-2-carboxamide hydrochloride (1.06 g, 2.59 mmole), triethylamine (0.526 g., 5.2 mmole) and 30% Pd on Celite (0.6 g) were mixed in abs EtOH (200 ml) and hydrogenated in a Parr apparatus for 2½ hrs. (14 lb $H_2$ uptake). Workup and treatment with HClg in the usual manner (see example 12) gave the product (0.7 g., 71.8% mp 178°–186° d) after recrystallization from i-PrOH:$Et_2O$.

Anal. calc'd. for $C_{20}H_{24}N_2O_3.HCl$: C, 63.74; H, 6.69; N, 7.43; Cl, 9.41.
(Corrected for 0.29% $H_2O$) Found: C, 63.48; H, 6.61; N, 7.16; Cl, 9.28.

B.
cis-4-Phenyl-2-[N-(3-dimethylaminopropyl)-aminomethyl]-1,3-benzodioxan hydrochloride Substitution in the procedure of example 5b for the cis-6-chloro-N-methyl-4-phenyl-1,3-benzodioxan-2-carboxamide used therein of an equimolar quantity of BL-4981A produces the title compound.

EXAMPLE 15 trans-6-Chloro-4-phenyl-N-(3-piperidinopropyl)-1,3-benzodioxan-2-carboxamide hydrochloride Substitution in the procedure of example 11 for the dimethylaminopropylamine used therein of an equimolar quantity of 3-piperidinopropylamine produces the title compound.

EXAMPLE 16 trans-4-Phenyl-N-(2-morpholinoethyl)-1,3-benzodioxan-2-carboxamide hydrochloride Substitution in the procedure of example 11 for the dimethylaminopropylamine used therein of an equimolar quantity of 2-morpholinoethylamine produces the title product.

EXAMPLE 17 cis-6-Chloro-4-phenyl-N-(4-methylaminobutyl)-1,3-benzodioxan-2-carboxamide hydrochloride Substitution in the procedure of example 11 for the N,N-dimethylaminopropylamine used therein of an equimolar quantity of N-methylaminobutylamine produces the title compound.

EXAMPLE 18 cis-4-Phenyl-N-(2-diethylaminoethyl)-1,3-benzodioxan-2-carboxamide hydrochloride Substitution in the procedure of example 11 for the N,N-dimethylaminopropylamine used therein of an equimolar quantity of N,N-diethylaminoethylamine produces the title product.

We claim:
1. The compound having the formula

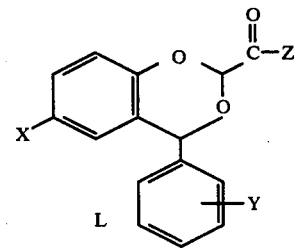

-continued
or

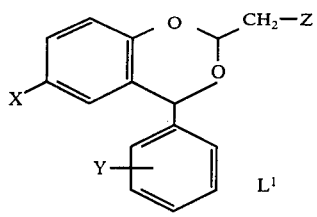

in which X and Y are alike or different and are H, F, Cl, Br, $CF_3$ or Nitro, Z is a radical having the formula

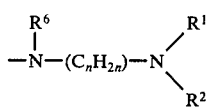

or

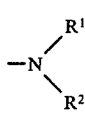

in which $R^6$ is H, (lower) alkyl or phenyl, $R^1$ and $R^2$ are alike or different and each is H, lower alkyl, cycloloweralkyl or when taken together with the nitrogen a heterocyclic ring having the formula

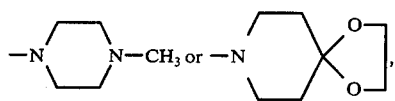

and n is an integer of 1 to 4 inclusive;
or a pharmaceutically acceptable acid addition salt thereof.

2. The compound of claim 1 having the formula

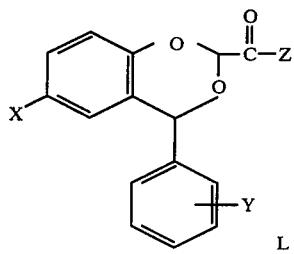

in which X and Y are alike or different and are H, F, Cl, Br, $CF_3$ or nitro, Z is a radical having the formula

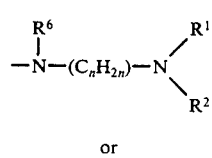

or

-continued

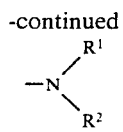

in which $R^6$ is H, (lower) alkyl or phenyl, $R^1$ and $R^2$ are alike or different and each is H, lower alkyl, cycloloweralkyl or when taken together with the nitrogen a heterocyclic ring having the formula

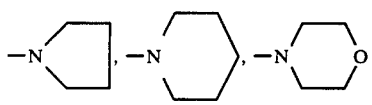

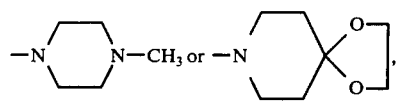

and n is an integer of 1 to 4 inclusive; or a pharmaceutically acceptable acid addition salt thereof.

3. The compound of claim 1 having the formula

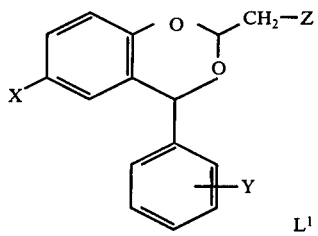

in which X and Y are alike or different and are H, F, Cl, Br, $CF_3$ or $NO_2$, and Z is a radical having the formula

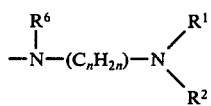

or

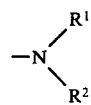

in which $R^6$ is H, (lower) alkyl or phenyl, $R^1$ and $R^2$ are alike or different and each is H, lower alkyl, cycloloweralkyl or when taken together with the nitrogen a heterocyclic ring having the formula

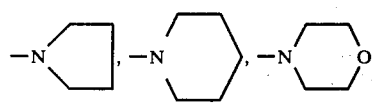

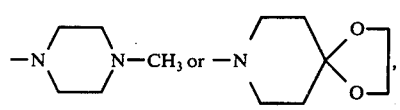

and n is an integer of 1 to 4 inclusive;
or a pharmaceutically acceptable acid addition salt thereof.

4. The compound of claim 1 having the formula

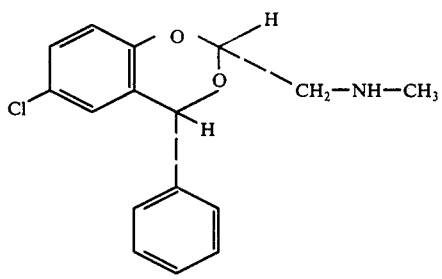

or the hydrochloride salt thereof.

5. The compound of claim 1 having the formula

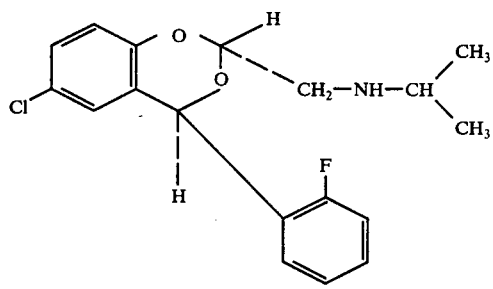

or the hydrochloride salt thereof.

6. The compound of claim 1 having the formula

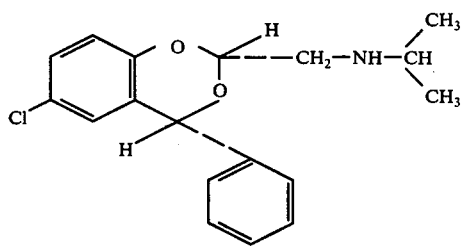

or the hydrochloride salt thereof.

7. The compound of claim 1 having the formula

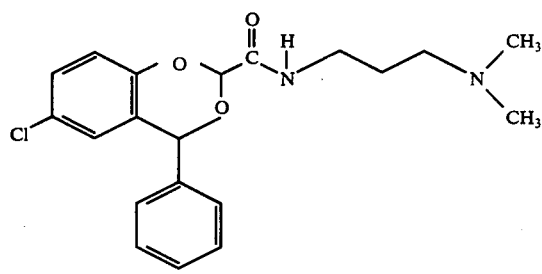

or a pharmaceutically acceptable acid addition salt thereof.

8. The compound of claim 1 having the formula

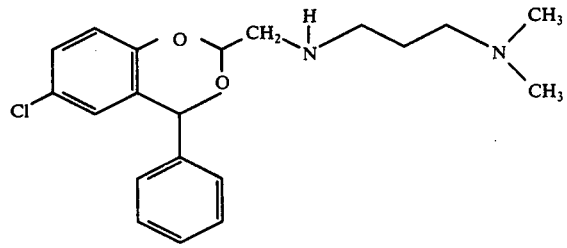

or a pharmaceutically acceptable acid addition salt thereof.

9. The compound of claim 1 having the formula

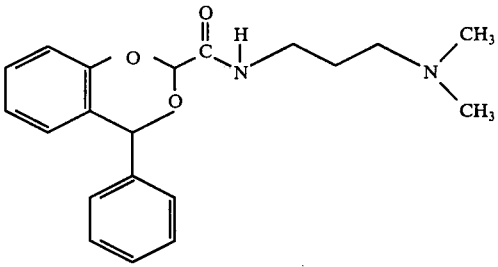

or a pharmaceutically acceptable acid addition salt thereof.

10. The compound of claim 1 having the formula

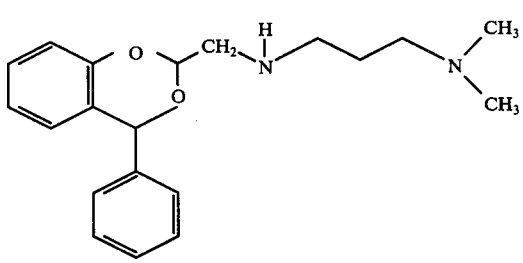

or a pharmaceutically acceptable acid addition salt thereof.

11. The cis isomer of the compound of claim 7.
12. The cis isomer of the compound of claim 8.
13. The cis isomer of the compound of claim 9.
14. The cis isomer of the compound of claim 10.
15. The compound of claim 1 having the formula

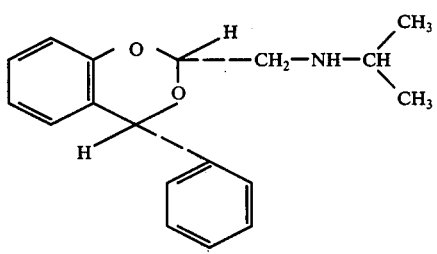

or the hydrochloride salt thereof.

16. The compound of claim 1 having the formula

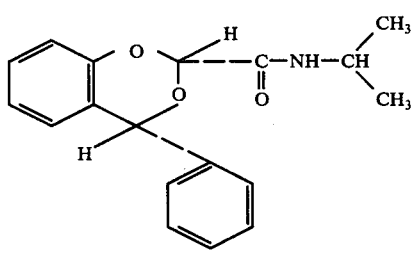

or the hydrochloride salt thereof.

17. The trans isomer of the compound of claim 7.
18. The trans isomer of the compound of claim 8.
19. The trans isomer of the compound of claim 9.
20. The trans isomer of the compound of claim 10.

* * * * *